(12) United States Patent
Tsunoda

(10) Patent No.: US 12,150,843 B2
(45) Date of Patent: Nov. 26, 2024

(54) STRETCHABLE MEMBER AND DISPOSABLE WEARABLE ARTICLE HAVING STRETCHABLE MEMBER

(71) Applicant: DAIO PAPER CORPORATION, Ehime (JP)

(72) Inventor: Arika Tsunoda, Tochigi (JP)

(73) Assignee: Daio Paper Corporation, Ehime (JP)

( * ) Notice: Subject to any disclaimer, the term of this patent is extended or adjusted under 35 U.S.C. 154(b) by 723 days.

(21) Appl. No.: 17/422,936

(22) PCT Filed: Feb. 21, 2020

(86) PCT No.: PCT/JP2020/007036
§ 371 (c)(1),
(2) Date: Jul. 14, 2021

(87) PCT Pub. No.: WO2020/189178
PCT Pub. Date: Sep. 24, 2020

(65) Prior Publication Data
US 2022/0087878 A1 Mar. 24, 2022

(30) Foreign Application Priority Data
Mar. 18, 2019 (JP) .................................. 2019-050236

(51) Int. Cl.
*A61F 13/49* (2006.01)
*A61F 13/15* (2006.01)
(Continued)

(52) U.S. Cl.
CPC .. *A61F 13/49019* (2013.01); *A61F 13/15203* (2013.01); *B32B 3/266* (2013.01);
(Continued)

(58) Field of Classification Search
CPC .......... A61F 13/15; A61F 13/49; A61F 13/51; A61F 13/514; B32B 7/022; B32B 29/02;
(Continued)

(56) References Cited

U.S. PATENT DOCUMENTS 11,045,360 B2 * 6/2021 Furuhashi ............. A61F 13/532
11,103,389 B2 * 8/2021 Takahashi ........... B29C 66/7294
(Continued)

FOREIGN PATENT DOCUMENTS

| CN | 107072835 | | 8/2017 |
|---|---|---|---|
| CN | 108348370 | A | 7/2018 |

(Continued)

OTHER PUBLICATIONS

1 The International Search Report for PCT/JP2020/007036, dated Apr. 7, 2020.

*Primary Examiner* — Michele Kidwell
(74) *Attorney, Agent, or Firm* — Andrus Intellectual Property Law, LLP

(57) ABSTRACT

A stretchable member has a second sheet layer with an exposed portion, first sheet layer, and elastic sheet interposed therebetween. The second and the first sheet layers are joined at multiple sheet joining portions arranged at intervals through joining holes penetrating the elastic sheet or via the elastic sheet, and vent holes each opened at least in a spread state by displacement of the edge of each joining hole away from the circumferential edge of each sheet joining portion in the stretchable direction ED. The colors of the external surface of the elastic sheet and of portions of the external surface of the first sheet layer observed through the vent holes are observable through the second sheet layer, and the color difference ΔE between the colors of the external surface of the elastic sheet and of the external surface of the first sheet layer is 30 or more.

12 Claims, 26 Drawing Sheets

(51) Int. Cl.
  *B32B 3/26* (2006.01)
  *B32B 7/022* (2019.01)
  *B32B 7/023* (2019.01)

(52) U.S. Cl.
  CPC .............. *B32B 7/022* (2019.01); *B32B 7/023* (2019.01); *A61F 2013/15243* (2013.01); *A61F 2013/15552* (2013.01); *A61F 2013/49038* (2013.01); *B32B 2555/02* (2013.01)

(58) Field of Classification Search
  CPC .... B32B 3/04; B32B 3/30; B32B 5/02; B32B 3/26
  See application file for complete search history.

(56) References Cited

U.S. PATENT DOCUMENTS

| | | | |
|---|---|---|---|
| 11,266,550 B2* | 3/2022 | Takaishi | B29D 99/0064 |
| 11,540,956 B2* | 1/2023 | Takeuchi | B29C 66/83511 |
| 11,607,352 B2* | 3/2023 | Takahashi | B29C 65/086 |
| 2007/0110963 A1* | 5/2007 | Uehara | D21H 27/002 |
| | | | 428/156 |
| 2016/0129626 A1 | 5/2016 | Arora et al. | |
| 2017/0246047 A1* | 8/2017 | Ryu | A61F 13/49001 |
| 2017/0290713 A1* | 10/2017 | LaVon | A61F 13/42 |
| 2018/0028371 A1 | 2/2018 | Takaishi | |
| 2018/0147098 A1 | 5/2018 | Lindström | |
| 2022/0071817 A1* | 3/2022 | Tsunoda | A61F 13/51496 |

FOREIGN PATENT DOCUMENTS

| | | |
|---|---|---|
| JP | 2015-204982 | 11/2015 |
| JP | 2016-140477 | 8/2016 |
| JP | 2016-189931 | 11/2016 |
| JP | 2016-189932 | 11/2016 |
| JP | 2016-189933 | 11/2016 |
| JP | 2017-035412 | 2/2017 |
| JP | 2017-064224 | 4/2017 |
| JP | 2017-148169 | 8/2017 |
| JP | 2017-225508 | 12/2017 |
| JP | 2018-516654 | 6/2018 |
| JP | 2020-032071 | 3/2020 |
| WO | 2019/235244 | 12/2019 |

\* cited by examiner

[FIG.1]
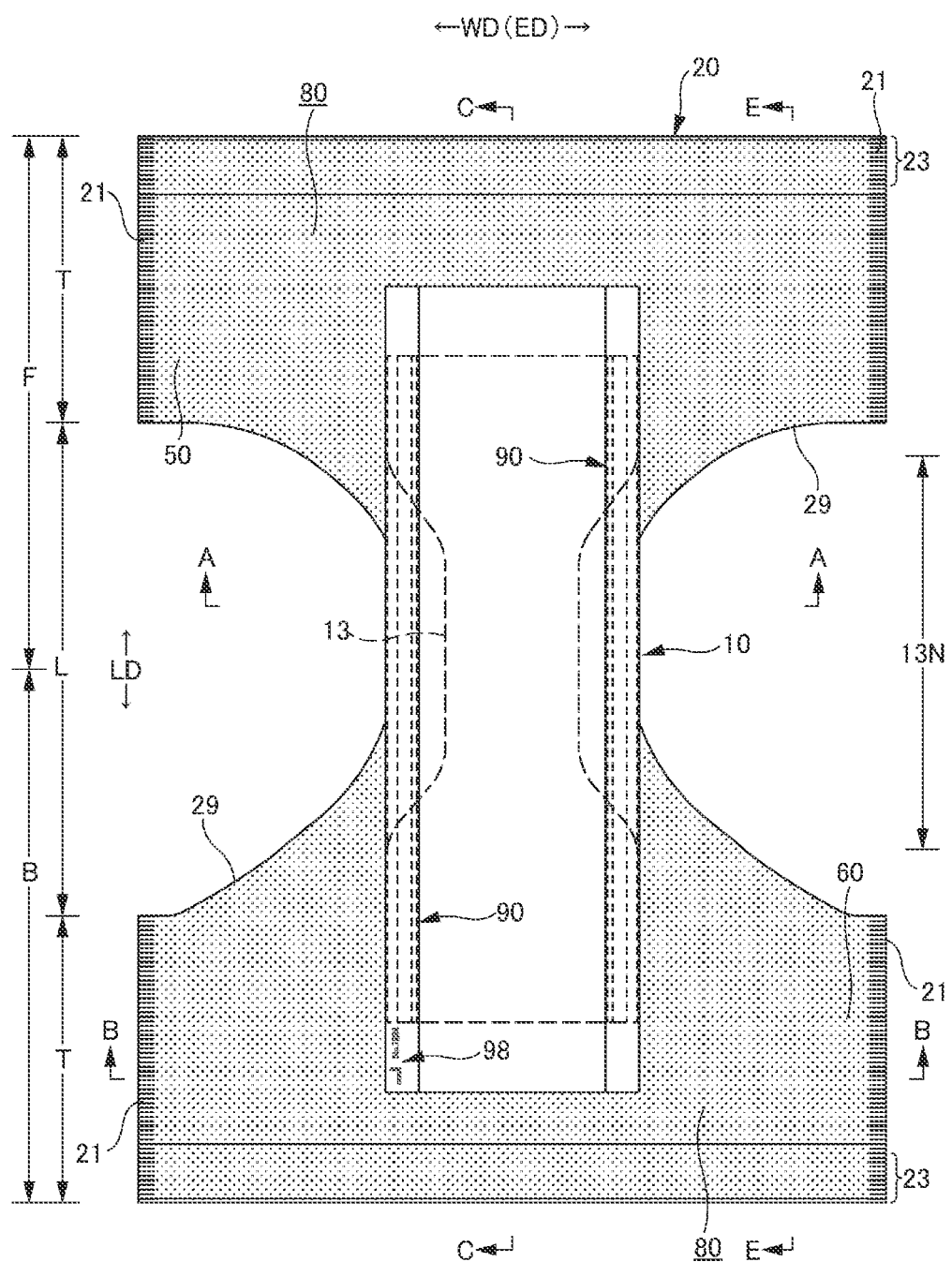

[FIG.2]
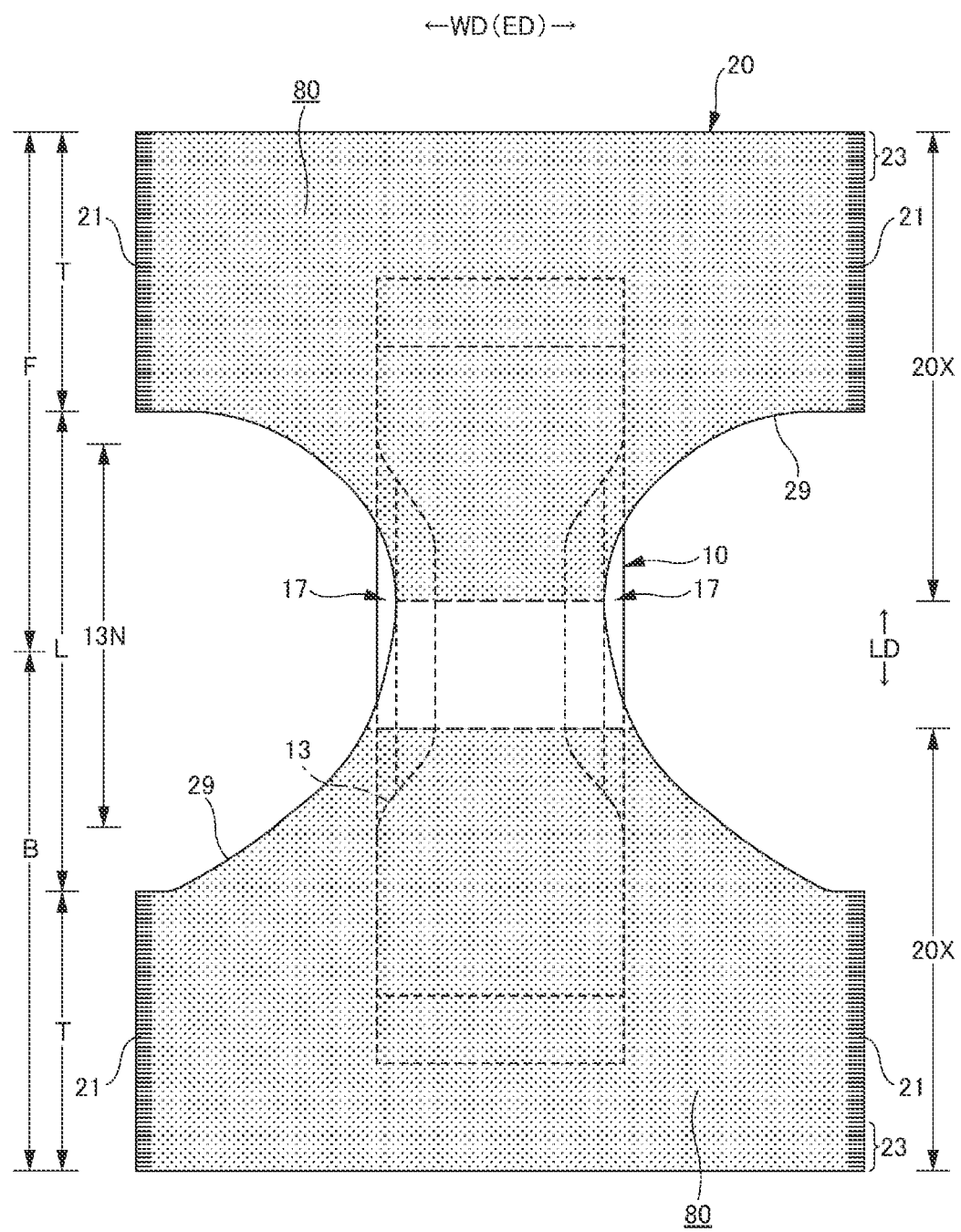

[FIG.3]
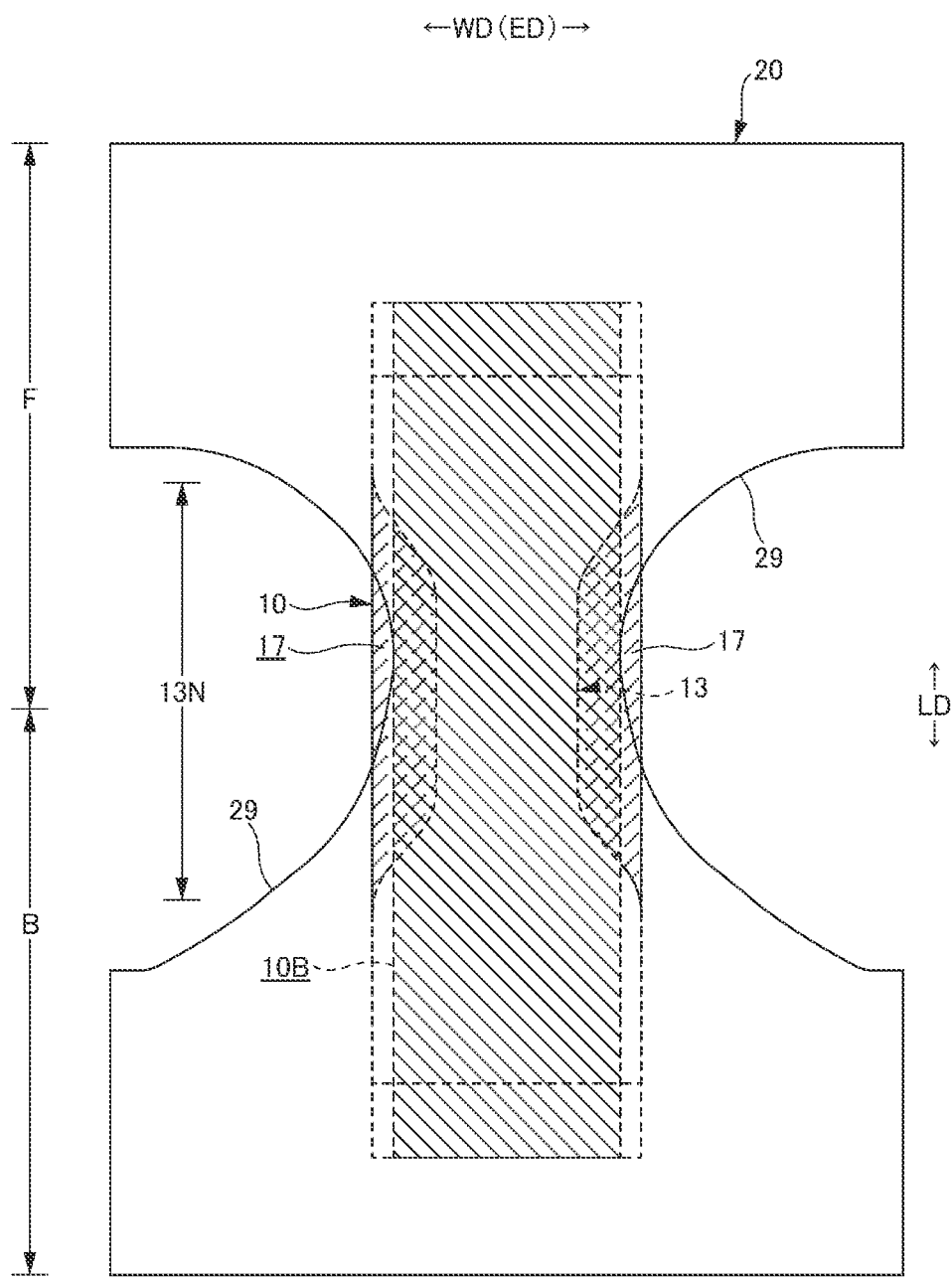

[FIG.4]
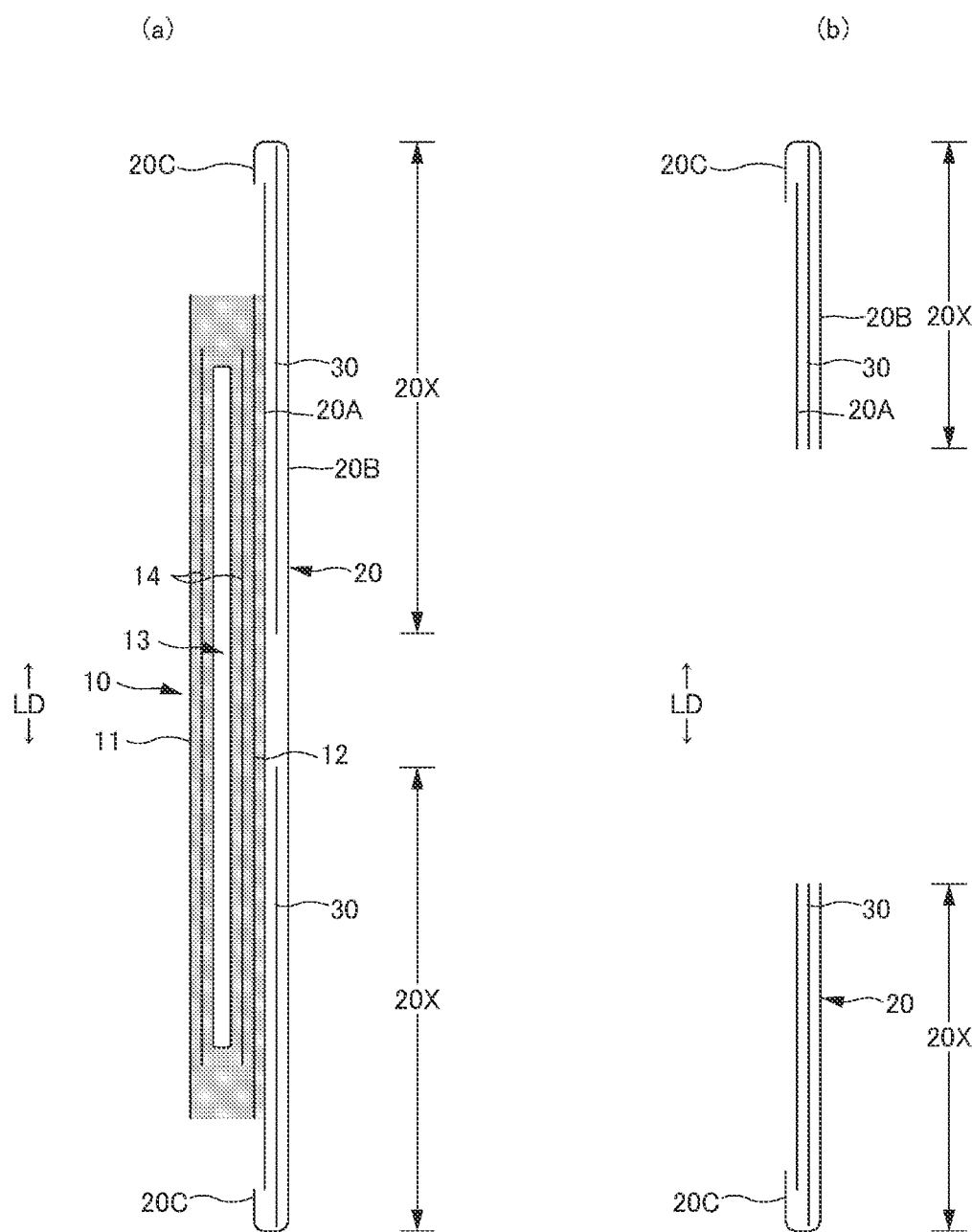

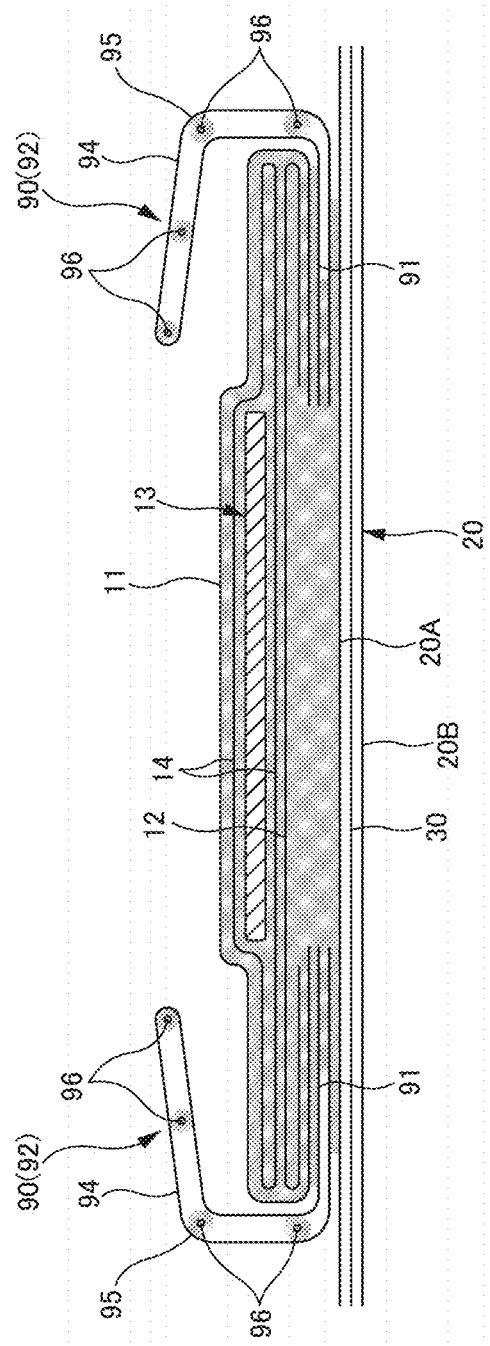

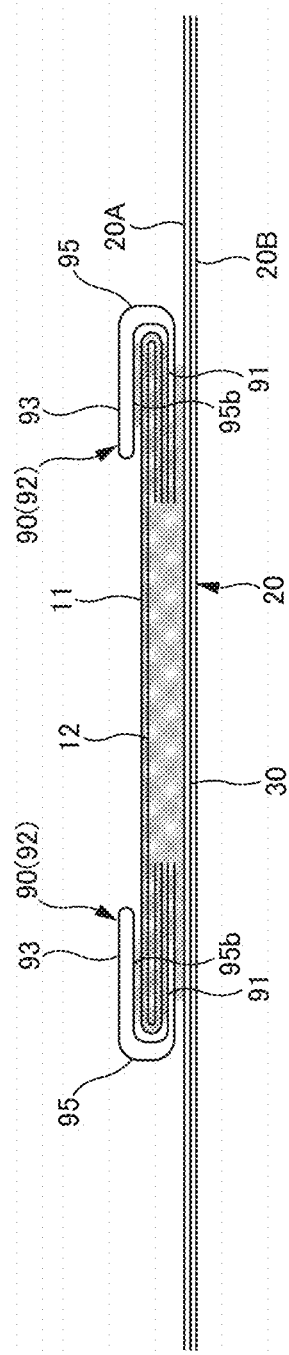

[FIG.7]
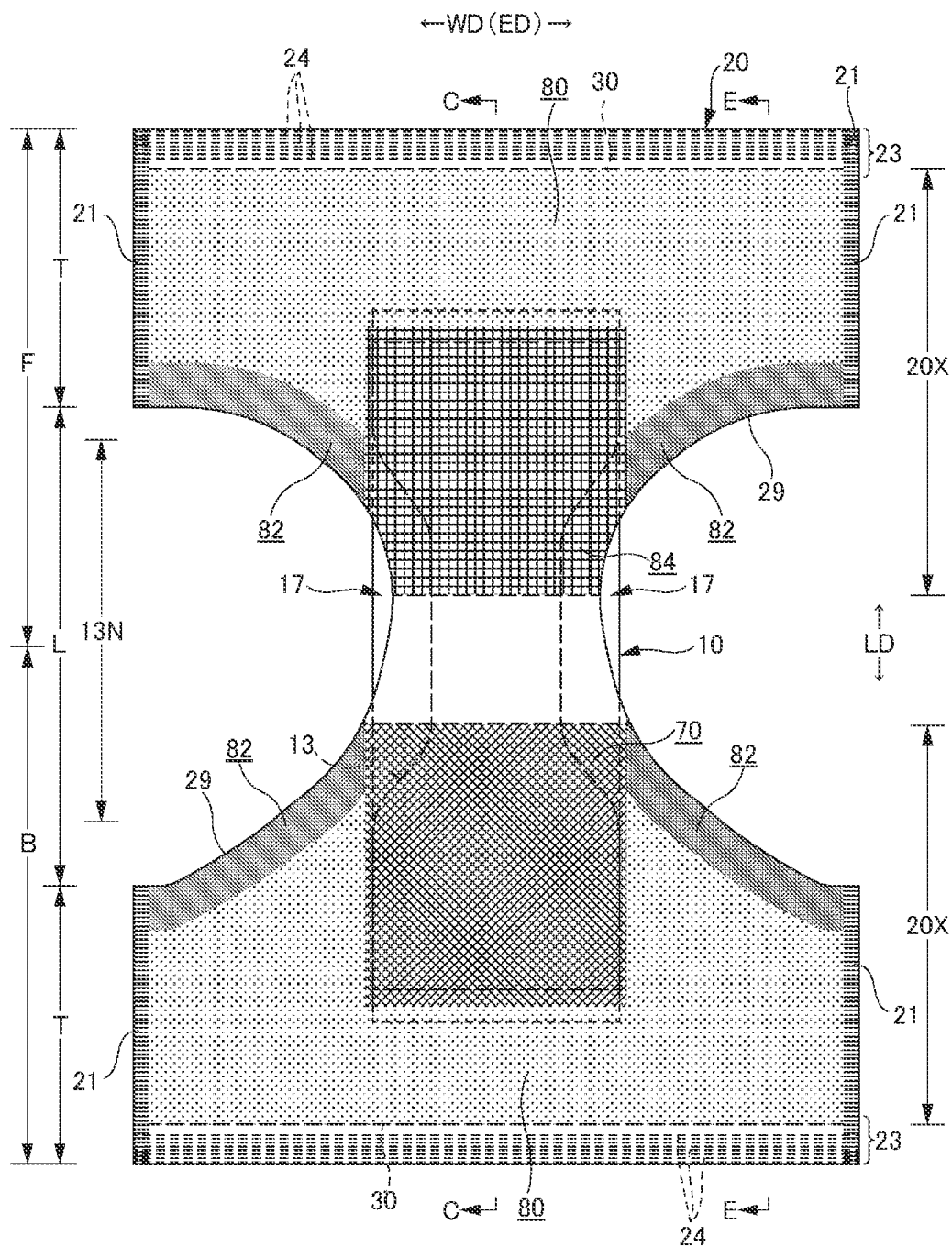

[FIG.8]
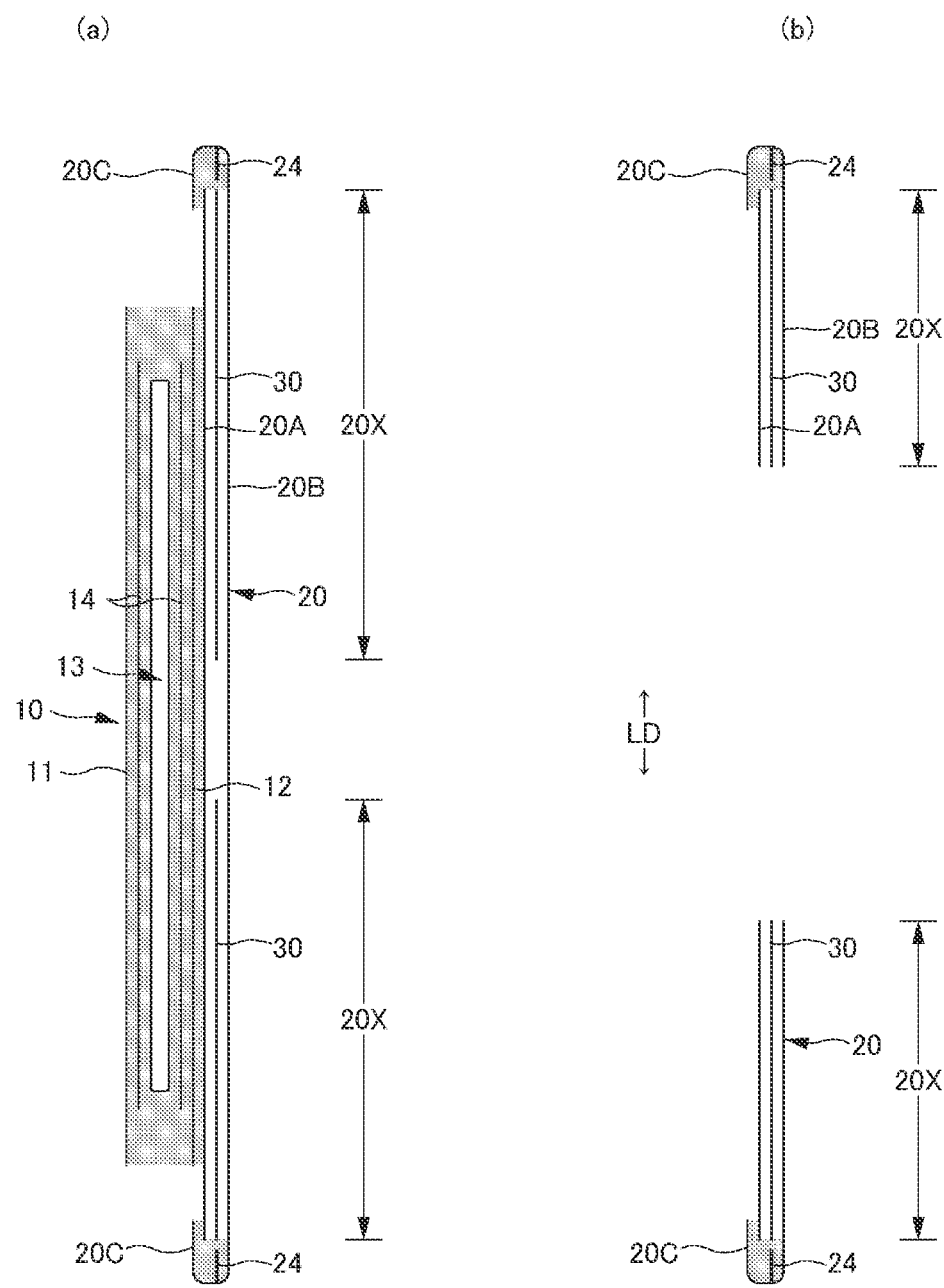

[FIG.9]
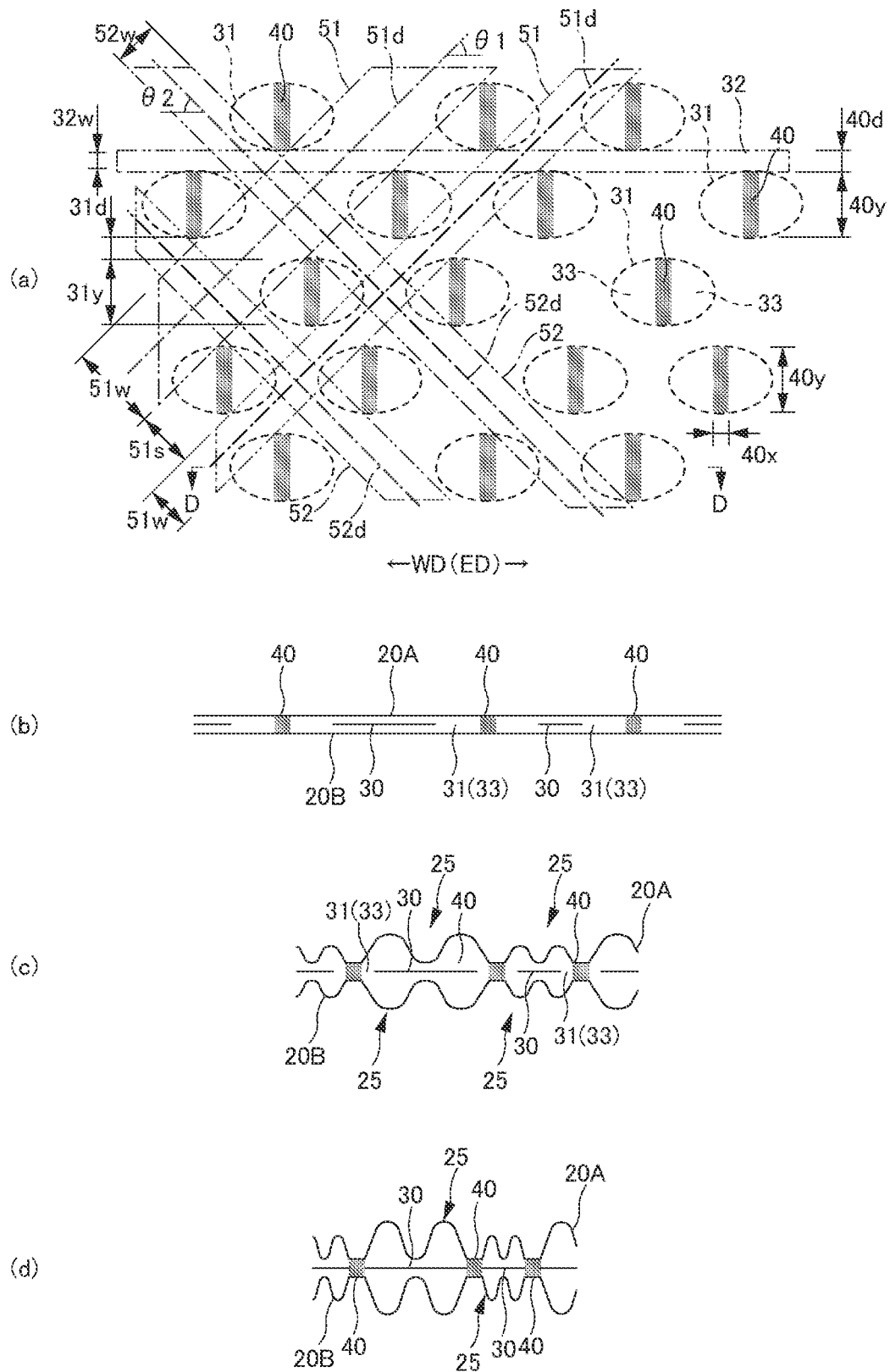

[FIG.10]
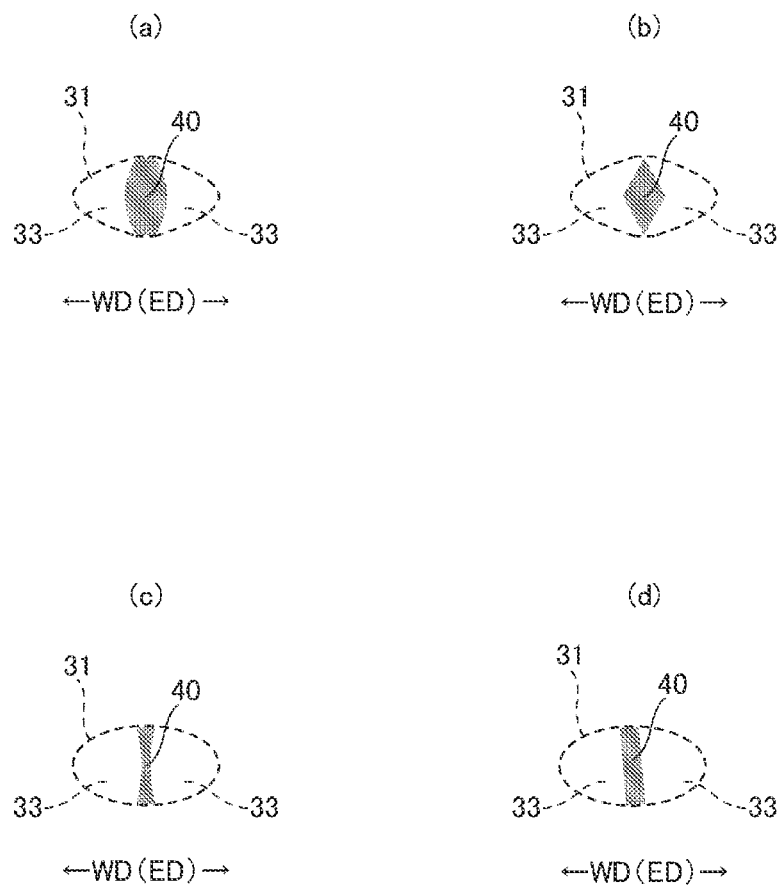

[FIG.11]
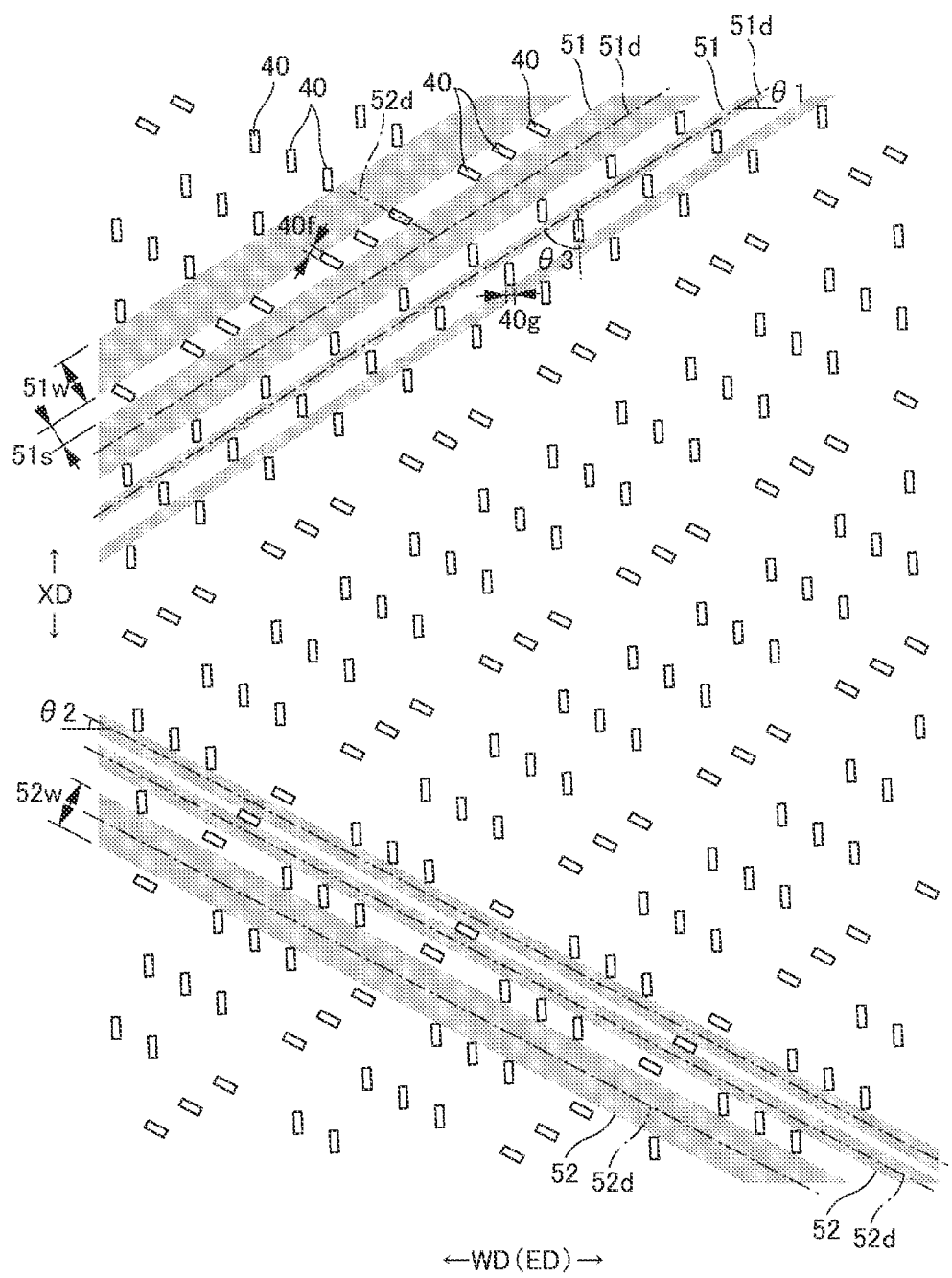

[FIG.12]
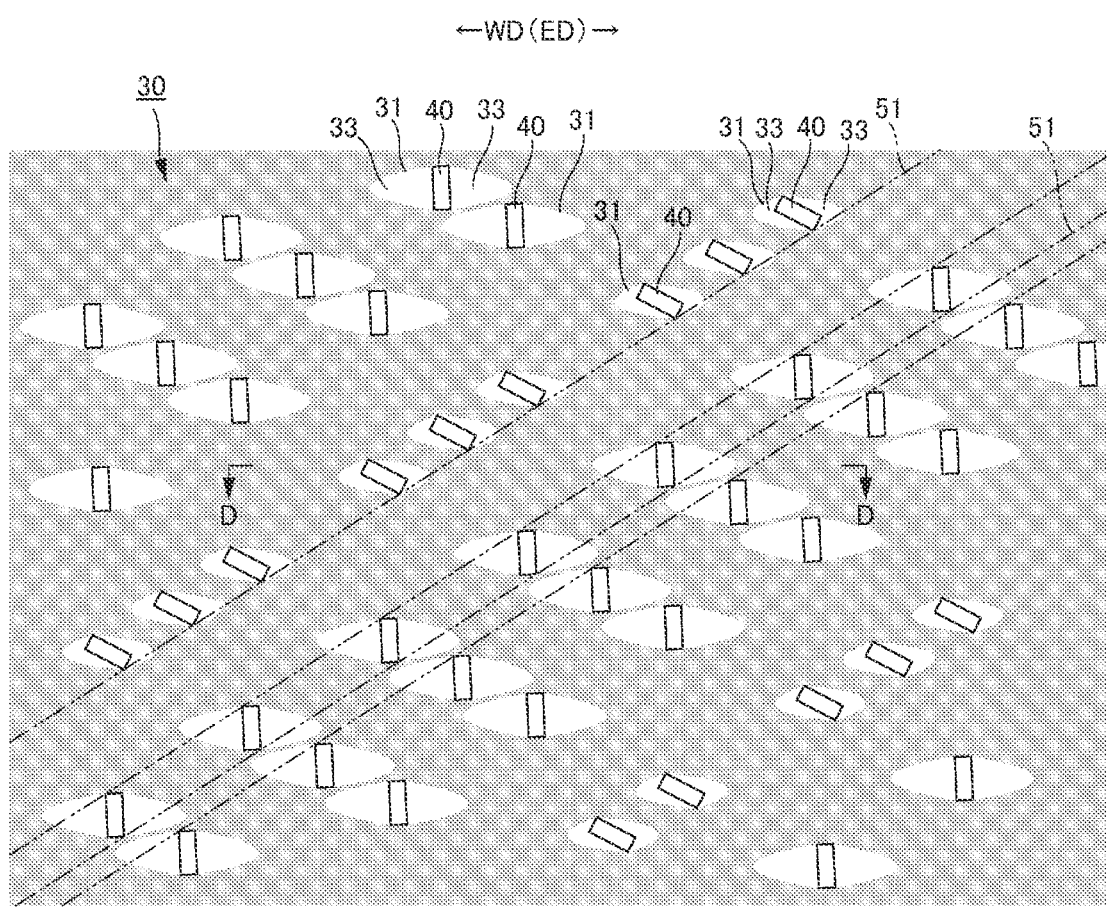

[FIG.13]
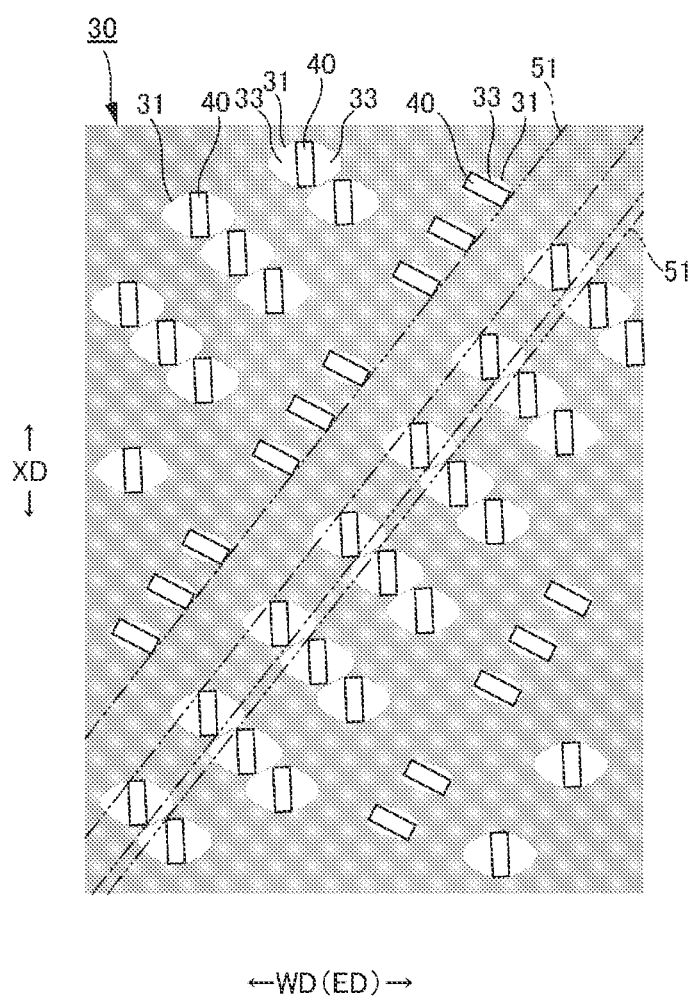

[FIG.14]
(a)
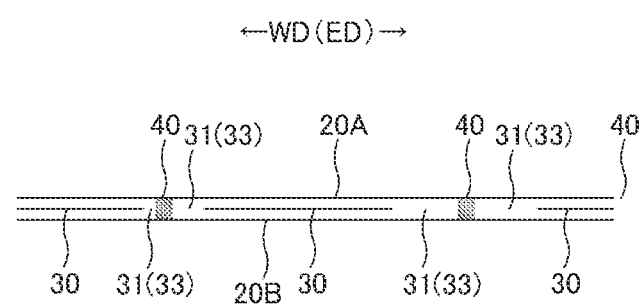
(b)
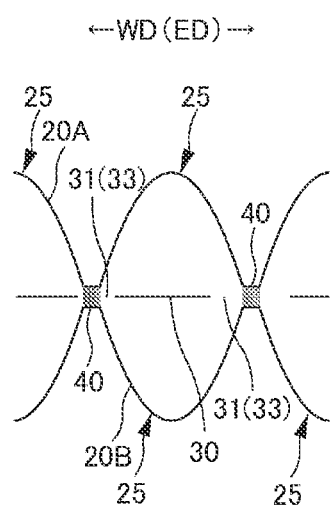

[FIG.15]
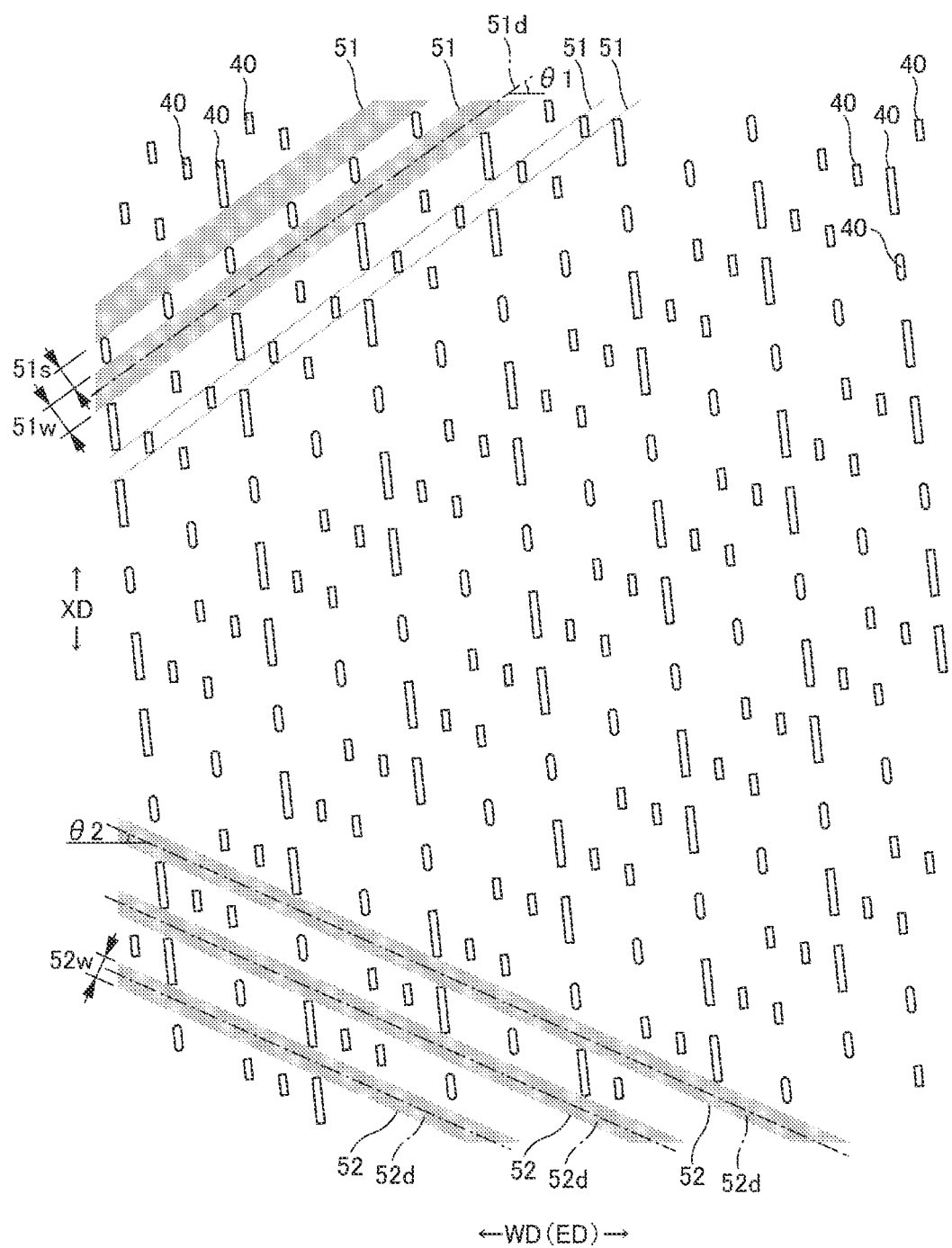

[FIG.16]
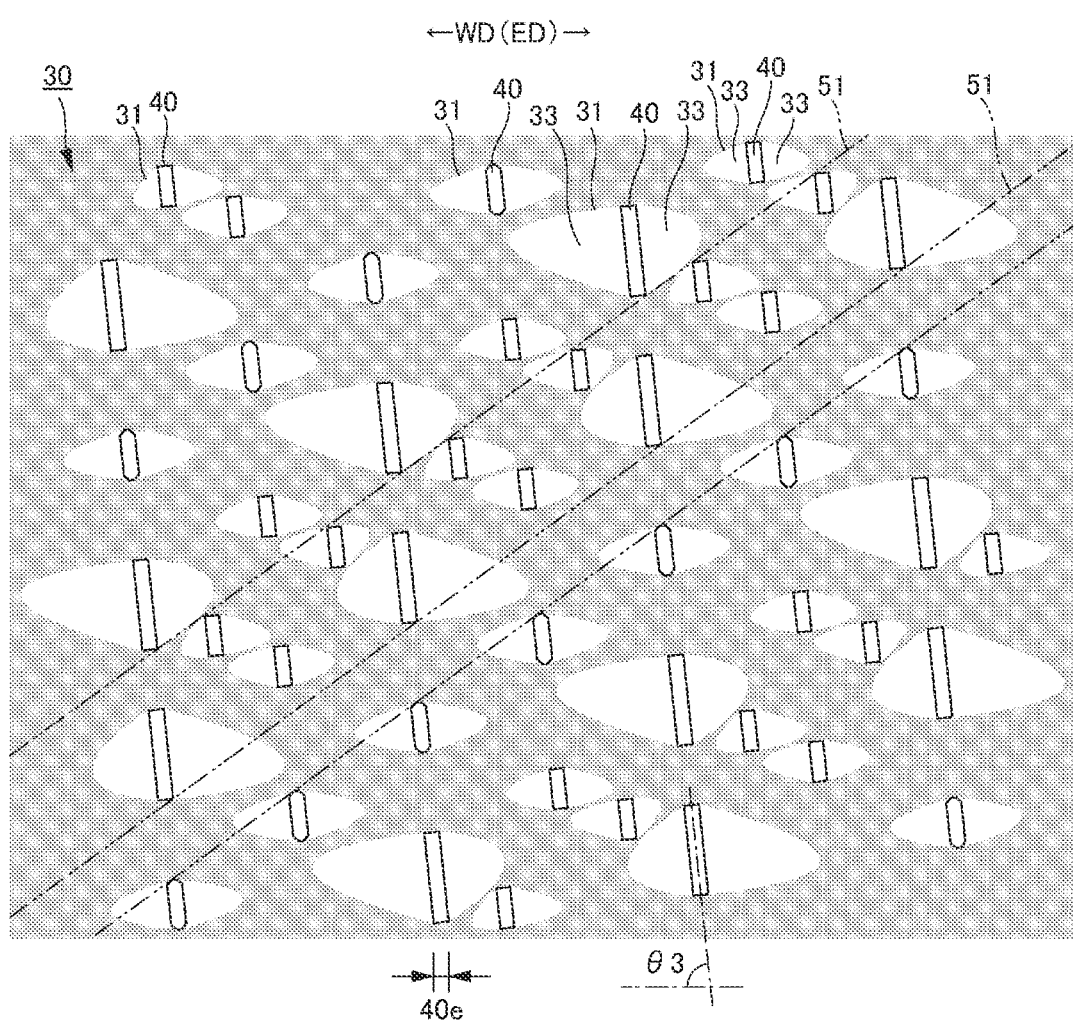

[FIG.17]
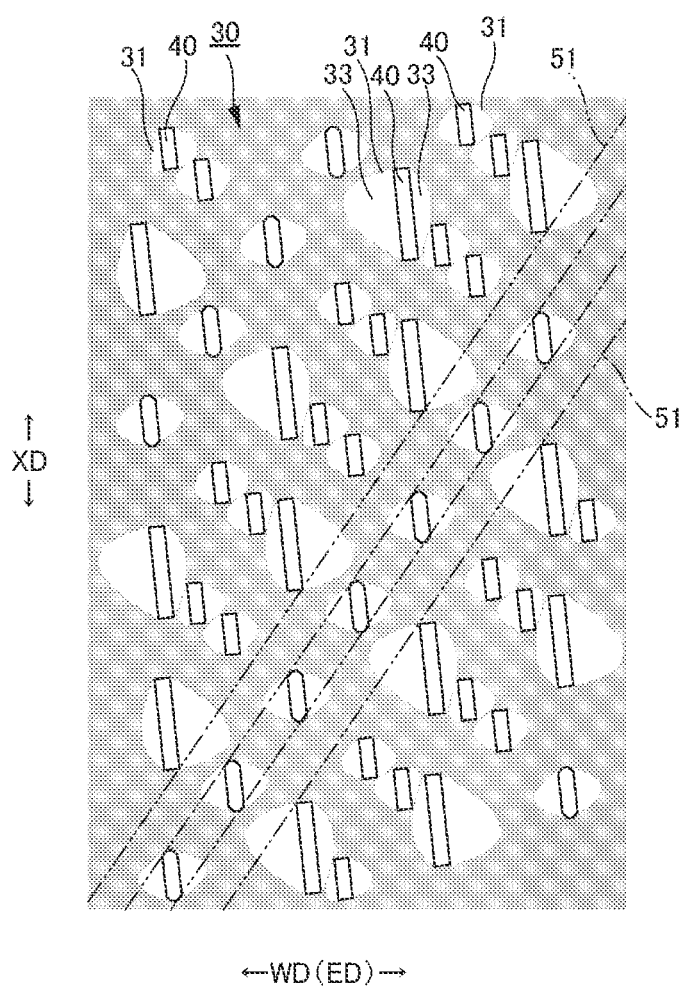

[FIG.18]
(a)
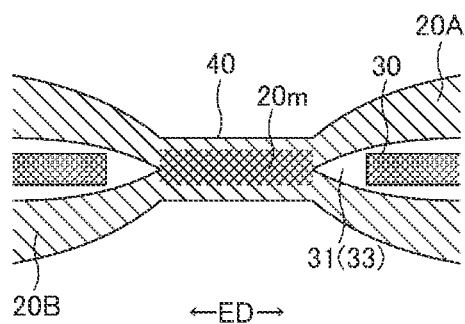
(b)
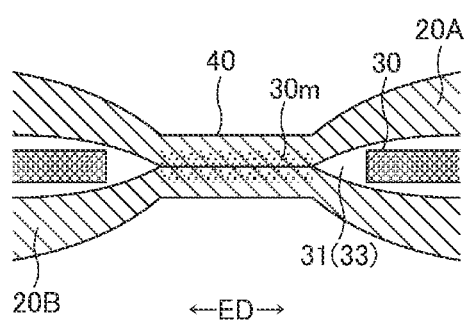
(c)
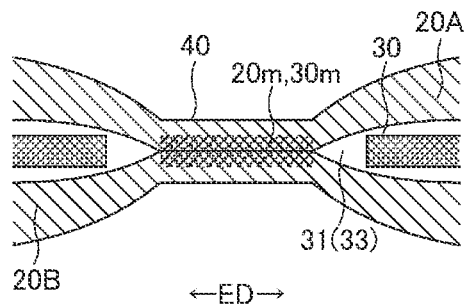

[FIG.19]
(a)
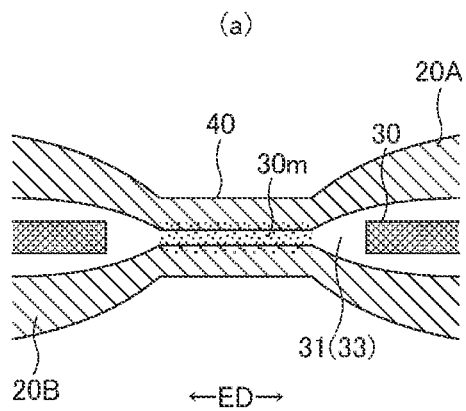
(b)
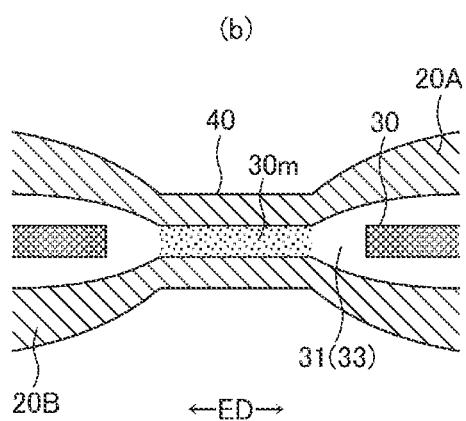
(c)
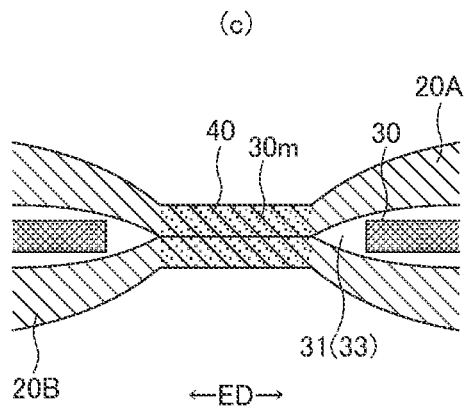

[FIG.20]
(a)
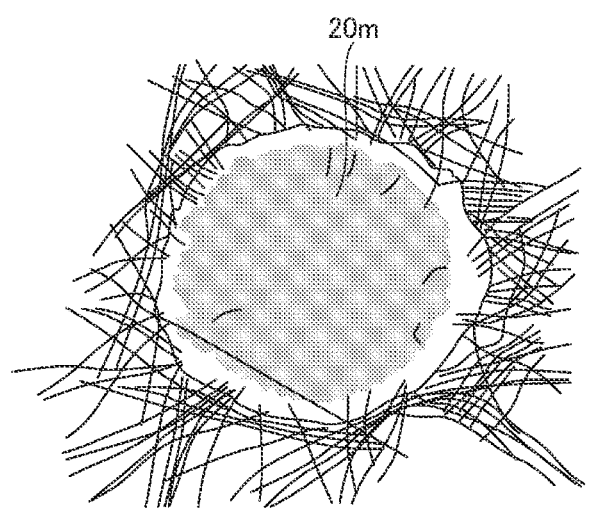
(b)
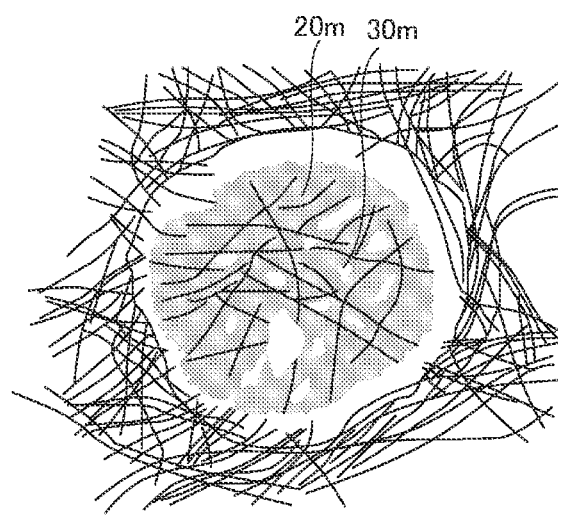

[FIG.21]
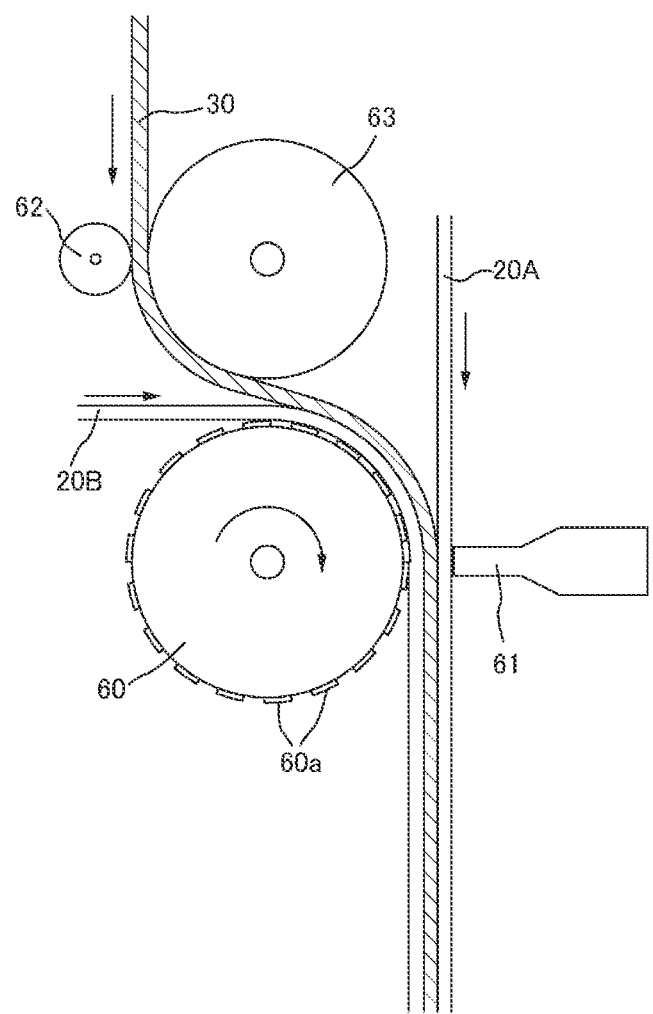

[FIG.22]
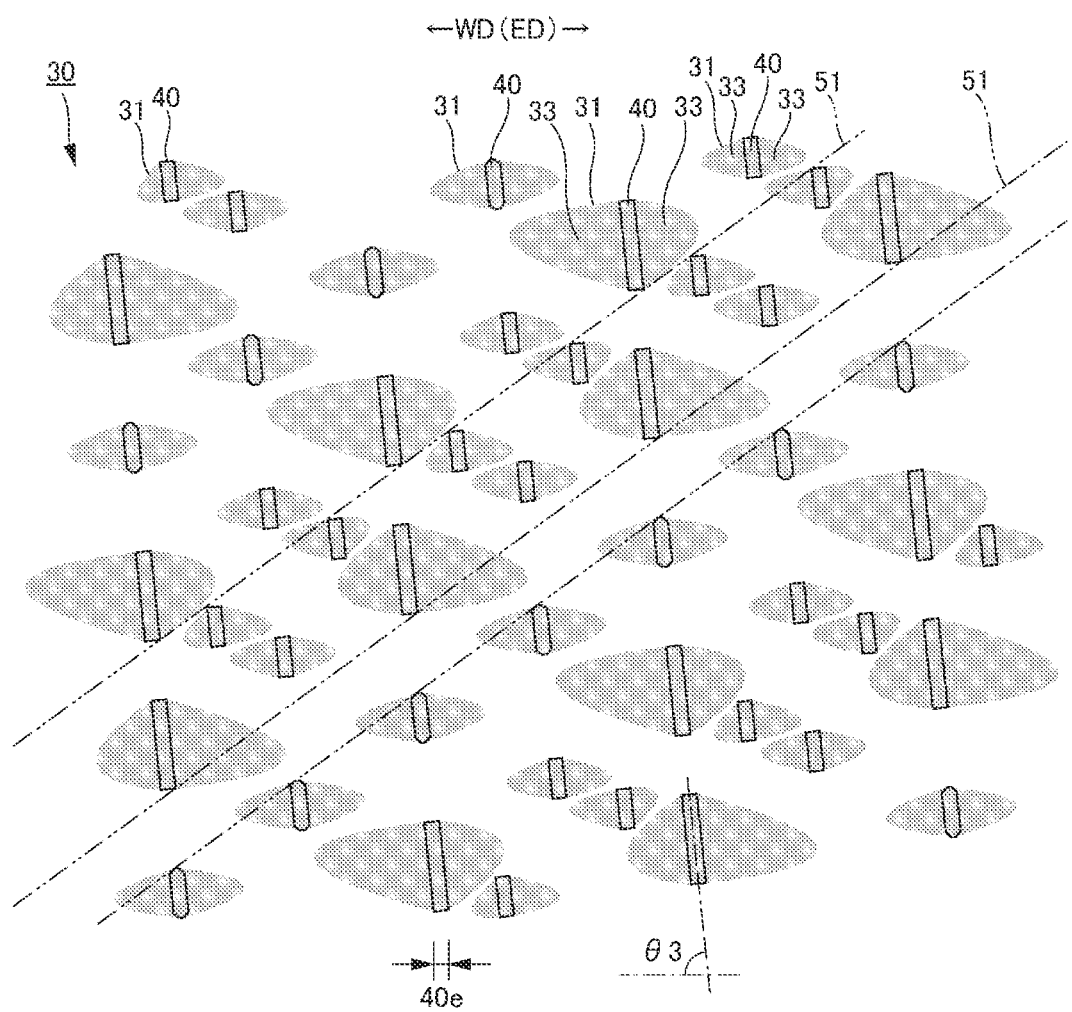

[FIG.23]
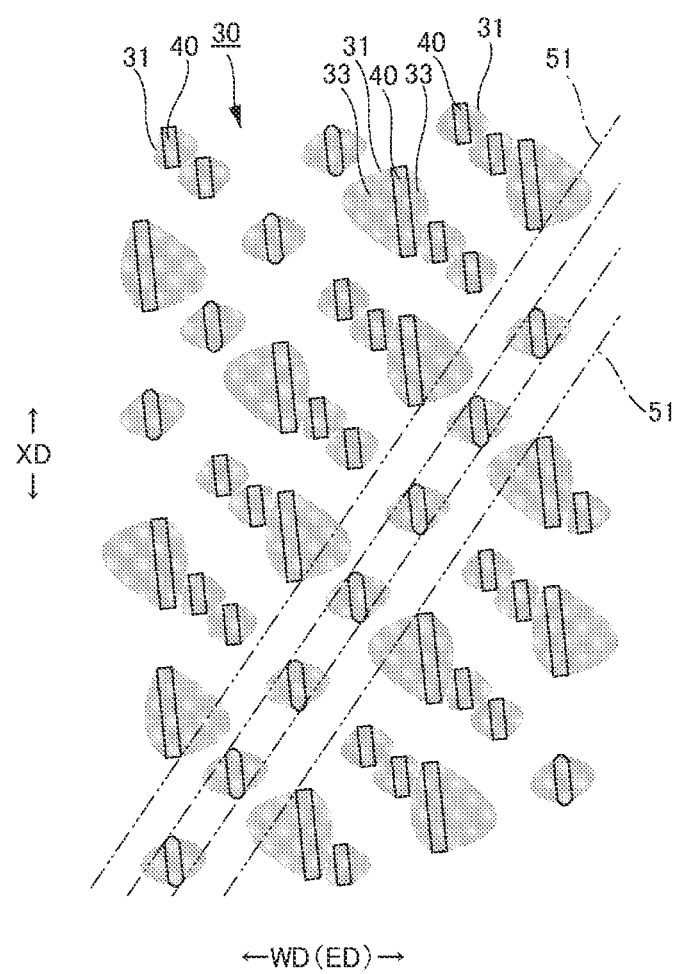

[FIG.24]
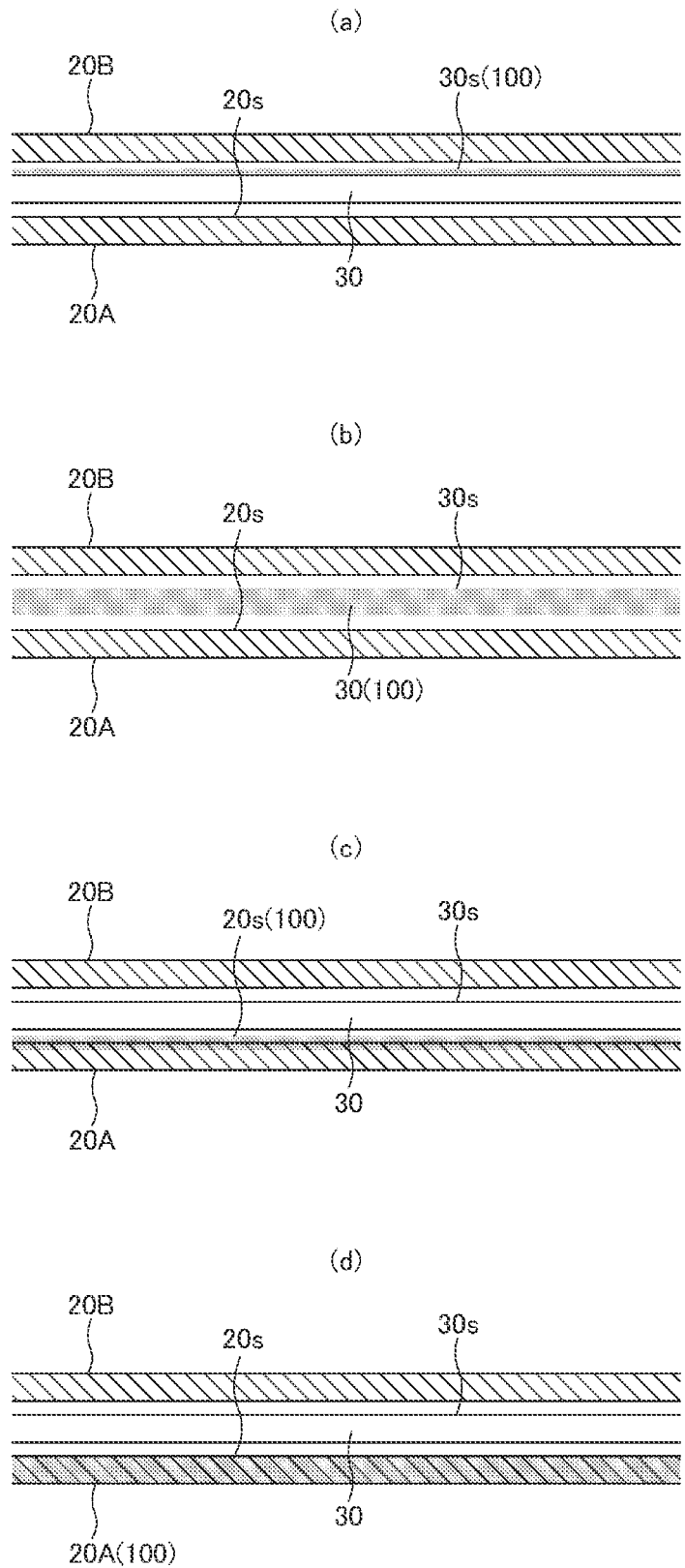

[FIG.25]
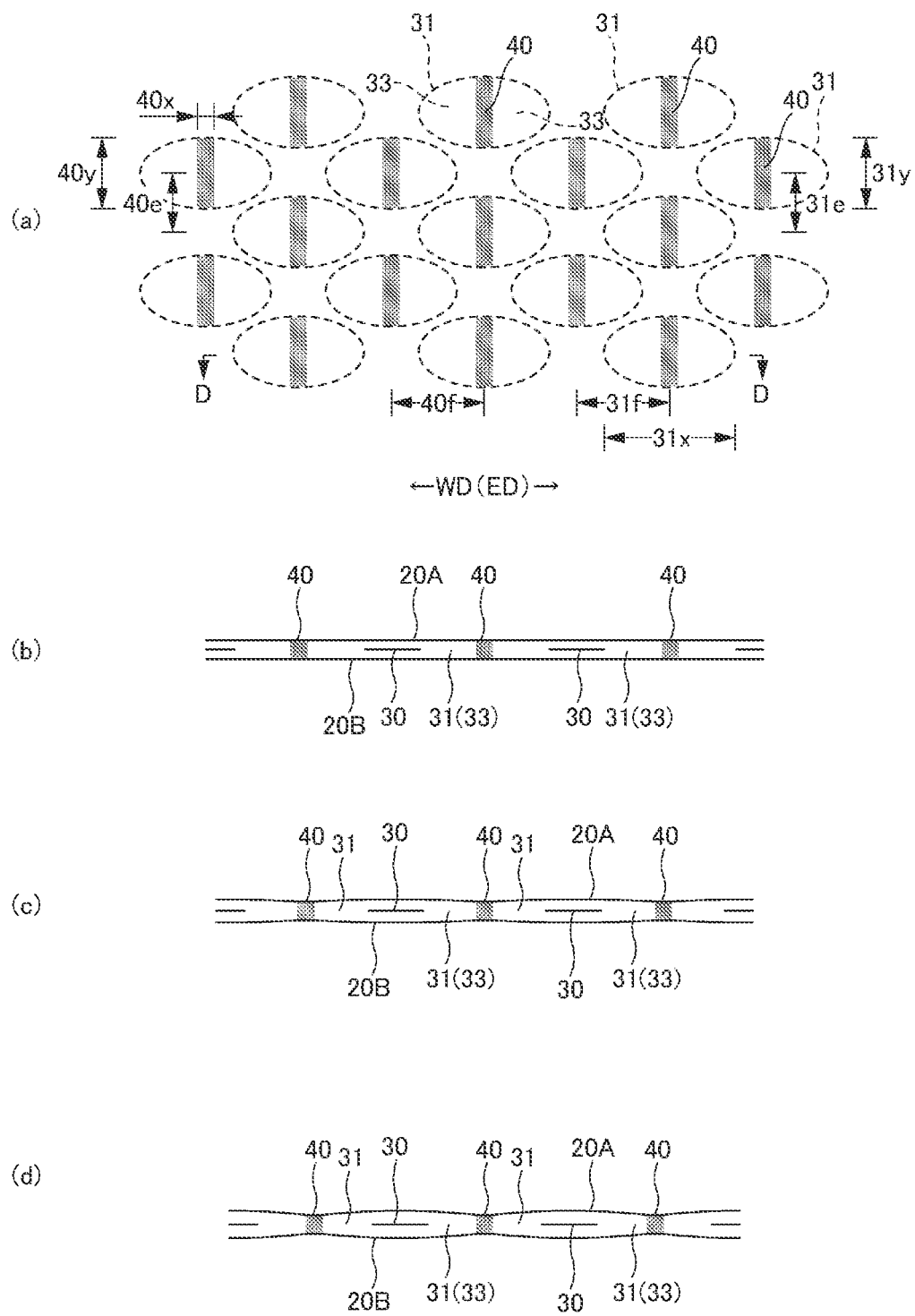

[FIG.26]
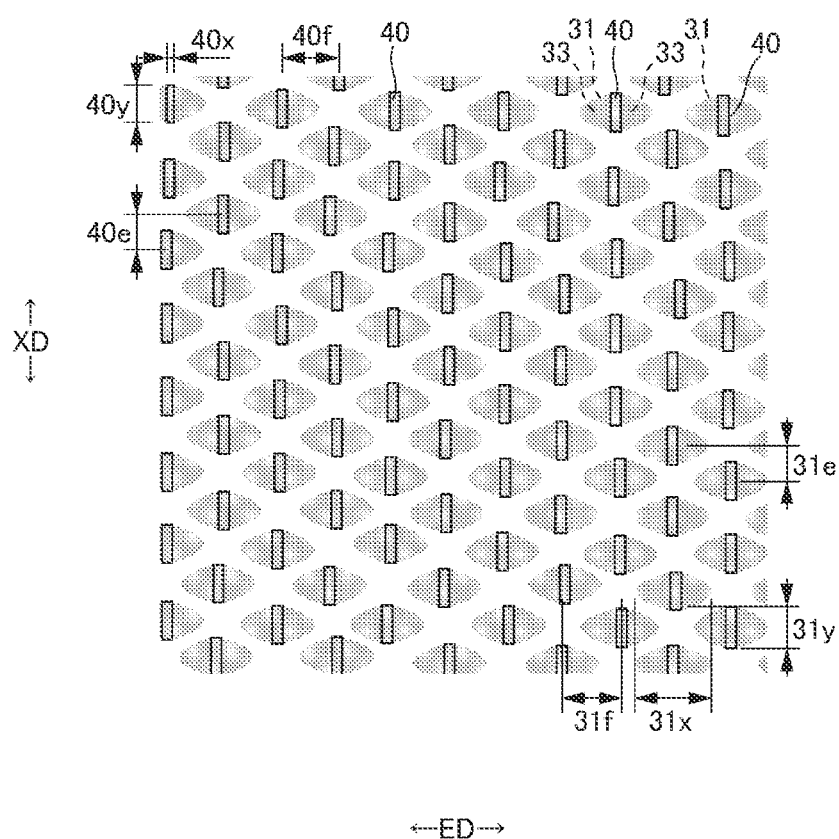

STRETCHABLE MEMBER AND DISPOSABLE WEARABLE ARTICLE HAVING STRETCHABLE MEMBER

CROSS-REFERENCE TO RELATED APPLICATIONS

This application is the U.S. national stage application of International Application PCT/JP2020/007036, filed Feb. 21, 2020, which international application was published on Sep. 24, 2020, as International Publication WO 2020/189178 in the Japanese language. The International Application claims priority of Japanese Patent Application No. 2019-050236, filed Mar. 18, 2019. The international application and Japanese application are both incorporated herein by reference, in entirety.

TECHNICAL FIELD

The present invention relates to a stretchable member having a stretchable structure wherein an elastic sheet, such as an elastic film, is interposed between first and second sheet layers, as well as to a disposable wearable article having the stretchable member.

BACKGROUND ART

In disposable wearable articles, such as disposable diapers, it is a common practice to impart stretchability where necessary, like around the legs or around the lower torso, to improve fitting on the body surface. For imparting stretchability, elongate elastic members, such as rubber threads, have conventionally been used widely, which are attached in a longitudinally stretched state. For imparting stretchability over a certain width, the rubber threads are fixed at intervals in the width direction. Further, there has also been proposed, as means for excellent plane fitting, to attach an elastic sheet in a state stretched in the direction for imparting stretchability. See, for example, Patent Literatures 1 and 2.

A stretchable member including such an elastic sheet is formed by interposing the elastic film between first and second sheet layers and joining, with the elastic film stretched in the stretchable direction, the first and second sheet layers through joining holes formed in the elastic film at multiple dot-shaped sheet joining portions arranged at intervals in the stretchable direction and the direction orthogonal thereto. In this stretchable member, in its natural length state, the intervals between the sheet joining portions are narrowed as the elastic sheet between the sheet joining portions contracts, to form ridges extending in the direction intersecting the stretchable direction between the sheet joining portions of the first and second sheet layers. On the other hand, in the stretched state, the intervals between the sheet joining portions and the ridges of the first and second sheet layers are expanded as the elastic sheet between the sheet joining portions stretches, to allow elastic stretching of the first and second sheet layers to the completely spread state. A stretchable region with such an elastic sheet has an advantage not only of excellent plane fitting, but also of remarkable flexibility due to the absence of joining between the elastic sheet and the first and second sheet layers and quite a little joining between the first and second sheet layers, and the joining holes in the elastic sheet also contribute to the improvement in air permeability.

On the other hand, as the disposable wearable articles are used with or in place of underwear, the stretchable member used in the disposable wearable articles are demanded to have the appearance close to fabric, in addition to the functional requirements, such as air permeability, fitting, and flexibility.

However, on the conventional stretchable member including the elastic sheet, the sheet joining portions and the joining holes in the elastic film are basically arranged in a non-directional pattern, such as a staggered pattern, so that the stretchable member in essence is recognized as having a plain appearance even with the ridges formed thereon, and provides poor aesthetic appearance.

CITATION LIST

Patent Literature

Patent Literature 1: JP 2016-189932 A
Patent Literature 2: JP 2015-204982 A
Patent Literature 3: JP 2016-140477 A
Patent Literature 4: JP 2016-189931 A
Patent Literature 5: JP 2016-189933 A
Patent Literature 6: JP 2017-064224 A
Patent Literature 7: JP 2017-148169 A
Patent Literature 8: JP 2017-225508 A

SUMMARY OF INVENTION

Technical Problem

It is therefore a primary object of the present invention to improve the aesthetic appearance of a stretchable member including an elastic sheet.

Solution to Problem

The stretchable member and the disposable wearable article having the stretchable member solving the above problem are as follows.
<First Aspect>
A stretchable member including:
an elastic sheet stretchable structure having an outer sheet layer with an exposed portion, a base sheet layer, and an elastic sheet interposed therebetween, the outer sheet layer and the base sheet layer being joined through joining holes penetrating the elastic sheet or via the elastic sheet at multiple sheet joining portions arranged at intervals,
wherein a region having the elastic sheet stretchable structure has a stretchable region contracted in a stretchable direction due to contraction of the elastic sheet and stretchable in the stretchable direction,
vent holes each opened at least in a spread state by displacement of an edge of each joining hole away from a circumferential edge of each sheet joining portion in the stretchable direction,
wherein a color of an external surface of the elastic sheet and a color of portions of an external surface of the base sheet layer observed through the vent holes are observable through the outer sheet layer, and
wherein a color difference $\Delta E$ between the color of the external surface of the elastic sheet and the color of the external surface of the base sheet layer is 30 or more.

Function and Effect

Each vent hole opened in the present elastic sheet stretchable structure is part of each joining hole penetrating the elastic sheet and improves air permeability, so that visual observation of these vent holes by users means the same as imparting of functional aesthetic appearance to the product. With the above-mentioned elastic sheet stretchable structure, when the outer sheet layer is of a sheet having a certain translucency, such as of nonwoven fabric, the shape of the vent holes may be observed faintly therethrough. However, with the conventional structure, the shape of the vent holes is not readily observable. In contrast, with the color difference ΔE of 30 or more between the color of the external surface of the elastic sheet and the color of the external surface of the base sheet layer as in the present stretchable member, the shape of the vent holes is readily observable through the outer sheet layer due to the difference between the color of the external surface of the elastic sheet and the color of the portions of the external surface of the base sheet layer observable through the vent holes. As a result, the aesthetic appearance of the present stretchable member is improved.

<Second Aspect>

The stretchable member according to the first aspect, wherein a region of the external surface of the base sheet layer overlapping at least the exposed portion is entirely colored by printing, or the base sheet layer is colored by spin-dyeing, wherein coloring of the base sheet layer has a CIELAB $L^*$ value of 20 to 60, and an absolute value of at least one of $a^*$ and $b^*$ values is 0 to 40, and wherein the color of the external surface of the elastic sheet has a CIELAB $L^*$ value of 50 to 90, and an absolute value of at least one of $a^*$ and $b^*$ values is 0 to 40.

Function and Effect

The color of the external surface of the elastic sheet and the color of the external surface of the base sheet layer may suitably be decided. In the present stretchable member, the color of the external surface of the elastic sheet is white or a pale color close to white, while the color of the external surface of the base sheet layer is deeper than that of the elastic sheet, so that the vent holes are observed in a deeper color while the remaining portions are observed in a lighter color, resulting in a net-like appearance. Accordingly, the present stretchable member is suitable for imparting a light tone, due to the net-like continuity of white color or a pale color close to white. Further, it is also preferred that the present stretchable member may be realized simply by coloring the base sheet layer without coloring the elastic sheet.

<Third Aspect>

The stretchable member according to the first aspect, wherein a region of the external surface of the elastic sheet overlapping at least the exposed portion is entirely colored by printing, or the elastic sheet is colored by spin-dyeing, wherein coloring of the elastic sheet has a CIELAB $L^*$ value of 20 to 60, and an absolute value of at least one of $a^*$ and $b^*$ values is 0 to 40, and wherein the color of the external surface of the base sheet layer has a CIELAB $L^*$ value of 50 to 90, and an absolute value of at least one of $a^*$ and $b^*$ values is 0 to 40.

Function and Effect

The color of the external surface of the elastic sheet and the color of the external surface of the base sheet layer may suitably be decided. In the present stretchable member, the color of the external surface of the base sheet layer is white or a pale color close to white, while the color of the external surface of the elastic sheet is deeper than that of the base sheet layer, so that the vent holes are observed in a pale color while the remaining portions are observed in a deeper color, resulting in a net-like appearance. Accordingly, the present stretchable member is suitable for imparting a deep or dark tone, due to the net-like continuity of a deep color. Further, it is also preferred that the present stretchable member may be realized simply by coloring the elastic sheet without coloring the base sheet layer.

<Fourth Aspect>

The stretchable member according to any one of the first to third aspects, wherein the outer sheet layer is of nonwoven fabric having a transmittance of 50% or higher according to translucency provided in JIS L 1913: 2010 (JIS method).

Function and Effect

The translucency of the outer sheet layer is not particularly limited as long as the color of the external surface of the elastic sheet and the color of the portions of the external surface of the base sheet layer observed through the vent holes are observable through the outer sheet layer, and using nonwoven fabric having a transmittance of 50% or higher is preferred for excellent visibility of the shape of the vent holes.

<Fifth Aspect>

The stretchable member according to any one of the first to fourth aspects, wherein the vent holes in the stretchable region in its natural length are opened.

Function and Effect

Since the vent holes are formed by displacement of the edge of each joining hole away from the circumferential edge of each sheet joining portion in the stretchable direction, the vent holes are deformed as the elastic sheet stretches and become larger towards the spread state. Depending on the shape (for example, circular) of the sheet joining portions, the edge of the joining hole may be in close contact with the circumferential edge of the sheet joining portion in the natural length state to sometimes form no vent hole. Even in this case, in a certain stretched state, such as in a worn state, the vent holes are opened at least on both sides in the stretchable direction of the sheet joining portion as the joining hole is stretched in the stretchable direction. However, this kind of products are sold in the natural length state, and without the openings in the elastic sheet in the natural length state, the aesthetic appearance associated with improved air permeability cannot be perceived unless the products are stretched. Thus, it is preferred as in the present stretchable member that the vent holes in the stretchable region in its natural length are opened.

<Sixth Aspect>

The stretchable member according to the fifth aspect, wherein in the stretchable region in a spread state, as an unjoined zone wherein a portion without the sheet joining portions continuously extends, a first unjoined zone extending linearly continuously along a first direction intersecting the stretchable direction at an acute angle is repeatedly present at intervals in a direction orthogonal to the first direction, wherein multiple sheet joining portions and multiple joining holes are disposed at intervals between adjacent first unjoined zones in the stretchable region, wherein a unit structure including a plurality of first unjoined zones of different first widths is repeatedly present in a direction orthogonal to the first direction in the stretchable region, a first width being defined as a width in a direction orthogonal to the first direction, wherein in the stretchable region in a spread state, as an unjoined zone wherein a portion without the sheet joining portions continuously extends, a second unjoined zone extending linearly continuously along a second direction intersecting the stretchable direction at an acute angle is repeatedly present at intervals in a direction orthogonal to the second direction, wherein multiple sheet joining portions and multiple joining holes are disposed at intervals between adjacent second unjoined zones in the stretchable region, wherein a unit structure including a plurality of second unjoined zones of different second widths is repeatedly present in a direction orthogonal to the second direction in the stretchable region, a second width being defined as a width in a direction orthogonal to the second direction, wherein the first direction and the second direction have opposite positive/negative inclinations with respect to the stretchable direction, and wherein in a spread state of the stretchable region, acute angles of intersection between the stretchable direction and each of the first direction and the second direction is 5 to 45 degrees, respectively.

Function and Effect

In the present stretchable member, the elastic sheet is present in a diagonal lattice pattern (the first and second unjoined zones intersect obliquely with each other), which is readily observable due to the color difference discussed above, so that an excellent aesthetic appearance in the diagonal lattice pattern is imparted.

<Seventh Aspect>

A disposable wearable article including an outer member integrally extending from a front body to a back body or an outer member having separate front and back bodies, an inner member attached to an intermediate portion in a width direction of the outer member across front and back sides of a crotch portion, side seal portions each formed by joining each side portion of the outer member in the front body and each side portion of the outer member in the back body, and a waist opening and a pair of right and left leg openings, wherein the outer member in at least one of the front body and the back body is a stretchable member having the elastic sheet stretchable structure according to any one of the first to sixth aspects, the elastic sheet stretchable structure being arranged over a width direction area corresponding to an area between the side seal portions in at least part of a front-back direction area, with the stretchable direction of the stretchable region arranged in a width direction.

Function and Effect

The stretchable member discussed above is suitable for an outer member of an underpants-type disposable wearable article as in the present aspect.

Effect of the Invention

According to the present invention, advantages of improved aesthetic appearance of a stretchable member including an elastic sheet or the like are provided.

BRIEF DESCRIPTION OF DRAWINGS

FIG. 1 is a plan view of the underpants-type disposable diaper in the spread state (internal surface side).

FIG. 2 is a plan view of the underpants-type disposable diaper in the spread state (external surface side).

FIG. 3 is a plan view of the underpants-type disposable diaper in the spread state, showing only the relevant parts.

FIG. 4(a) is a sectional view taken along lines C-C in FIG. 1, and FIG. 4(b) is a sectional view taken along lines E-E in FIG. 1.

FIG. 5 is a cross-sectional view taken along lines A-A in FIG. 1.

FIG. 6 is a cross-sectional view taken along lines B-B in FIG. 1.

FIG. 7 is a plan view of the underpants-type disposable diaper in the spread state (external surface side).

FIG. 8(a) is a sectional view taken along lines C-C in FIG. 7, and FIG. 8(b) is a sectional view taken along lines E-E in FIG. 7.

FIG. 9(a) is a plan view of the relevant part of the stretchable region, FIG. 9(b) is a cross-sectional view taken along lines D-D in FIG. 9(a), FIG. 9(c) is the cross-sectional view in the worn state, and FIG. 9(d) is the cross-sectional view in the natural length state.

FIG. 10 illustrates plan views of the sheet joining portion in various shapes.

FIG. 11 is a plan view of the stretchable region in the spread state.

FIG. 12 is an enlarged plan view of the relevant part of the stretchable region in the spread state.

FIG. 13 is an enlarged plan view of the relevant part of the stretchable region in the natural length state.

FIG. 14 (a) is a cross-sectional view taken along lines D-D in FIG. 12, and FIG. 14 (b) is the cross-sectional view in the natural length state.

FIG. 15 is a plan view of the stretchable region in the spread state.

FIG. 16 is an enlarged plan view of the relevant part of the stretchable region in the spread state.

FIG. 17 is an enlarged plan view of the relevant part of the stretchable region in the natural length state.

FIG. 18 illustrates schematic cross-sectional views of the relevant cross section of the outer member stretched to some extent.

FIG. 19 illustrates schematic cross-sectional views of the relevant cross section of the outer member stretched to some extent.

FIG. 20(a) is a trace of a plan image of the sheet joining portion formed in the first weld mode, and FIG. 20(b) is a trace of a plan image of the sheet joining portion formed in the third weld mode.

FIG. 21 is a schematic view of ultrasonic sealing apparatus.

FIG. 22 is an enlarged plan view of the relevant part of the stretchable region in the spread state.

FIG. 23 is an enlarged plan view of the relevant part of the stretchable region in the natural length state.

FIG. 24 illustrates schematic cross-sectional views of the elastic sheet stretchable structure.

FIG. 25(a) is a plan view of the relevant part of the non-stretchable region, FIG. 25(b) is a cross-sectional view taken along lines D-D in FIG. 25(a), FIG. 25(c) is the cross-sectional view in the worn state, and FIG. 25(d) is the cross-sectional view in the natural length state.

FIG. 26 is a plan view of the relevant part of the non-stretchable region.

DESCRIPTION OF EMBODIMENTS

Embodiments of the disposable wearable articles will now be described in detail with reference to the accompanying drawings. In the drawings, dotted pattern regions represent adhesives as joining means for joining the components on the front or back surface side of the respective regions, and may be formed by, for example, solid, bead, curtain, summit, or spiral application, or pattern coating (transfer of a hot melt adhesive by relief printing) of a hot melt adhesive, and fixed portions of the elastic member may be formed, in place of or in addition to this, by application of a hot melt adhesive to the external surface of the elastic member with a comb gun or a surewrap. Examples of the hot melt adhesive include, but not limited to, EVA-based, adherent rubber-based (elastomer-based), polyolefin-based, and polyester/polyamide-based adhesives. The joining means for joining the components may alternatively be material welding, such as heat sealing or ultrasonic sealing.

As the nonwoven fabric in the description hereinbelow, commonly known nonwoven fabric may suitably be used depending on the sites or purposes. Examples of the constituent fibers of the nonwoven fabric include, but not limited to, synthetic fibers, such as polyolefin-based, e.g., polyethylene or polypropylene, polyester-based, or polyamide-based fibers (including not only single component fibers, but also composite fibers, such as of core/sheath type), as well as regenerated fibers, such as rayon or cuprammonium, or natural fibers, such as cotton, and also mixtures thereof. For improved flexibility of the nonwoven fabric, the constituent fibers may preferably be crimped fibers. The constituent fibers of the nonwoven fabric may also be hydrophilic fibers (including those rendered hydrophilic with hydrophilizers), hydrophobic fibers, or water-repelling fibers (including those rendered water-repelling with water repellents). Further, nonwoven fabric may generally be categorized into short fiber nonwoven, long fiber nonwoven, spunbond nonwoven, melt blown nonwoven, spunlace nonwoven, thermal bonded (air through) nonwoven, needle-punched nonwoven, point-bonded nonwoven, composite nonwoven (SSS nonwoven fabric having the same or similar nonwoven layers laid one on top of another, as well as SMS or SMMS nonwoven fabric having different nonwoven layers laid one on top of another, i.e., melt blown layer interposed between spunbond layers), or the like nonwoven fabric, depending on the length of the fibers, method of forming the sheet, method of joining the fibers, or layered structure, and any of these nonwoven fabric may be used. The composite nonwoven fabric refers to those having all the layers integrally manufactured and subjected to fiber joining process all over the layers, and does not include those having a plurality of nonwoven fabric layers separately manufactured and bonded with joining means, such as hot melt adhesives.

FIGS. 1 to 6 show an underpants-type disposable diaper. Reference sign LD (longitudinal direction) denotes the front-back direction, and WD the width direction. This underpants-type disposable diaper (also referred to simply as the diaper hereinbelow) has outer member 20 forming front body F and back body B, and inner member 10 integrally fixed on the internal surface side of the outer member 20, and the inner member 10 has liquid pervious top sheet 11, liquid impervious sheet 12, and absorbent body 13 interposed therebetween. In production, the back surface of the inner member 10 is joined to the internal surface (upper surface) of the outer member 20 by joining means, such as a hot melt adhesive, then the inner and outer members 10, 20 are folded along the center of the front-back direction LD (longitudinal direction), which center is the boundary between the front body F and the back body B, and each side portion of the front body F and each side portion of the back body B are joined together by means of thermal welding or a hot melt adhesive to form side seal portions 21, to thereby obtain an underpants-type disposable diaper having a waist opening and a pair of right and left leg openings thus formed.

Structural Example of Inner Member

The inner member 10 has a structure, as shown in FIGS. 4 to 6, including top sheet 11, liquid impervious sheet 12 made of, for example, polyethylene, and absorbent body 13 interposed therebetween, to absorb and hold excrement liquid passing through the top sheet 11. The planar shape of the inner member 10 is not particularly limited, and may generally be approximately rectangular, as shown in FIG. 1.

As the top sheet 11 covering the front surface side (skin side) of the absorbent body 13, perforated or imperforate nonwoven fabric or a porous plastic sheet may preferably be used.

As the liquid impervious sheet 12 covering the back surface side (non-skin-contacting side) of the absorbent body 13, a liquid impervious plastic sheet, such as of polyethylene or polypropylene, may be used, and those having moisture permeability may preferably be used for preventing stuffiness, such as microporous sheets obtained by, for example, melting and kneading an inorganic filler in a polyolefin resin, such as polyethylene or polypropylene, forming the kneaded mixture into a sheet, and then uniaxially or biaxially drawing the sheet.

The absorbent body 13 may be a conventional one, for example, accumulated pulp fibers, an assembly of filaments, such as of cellulose acetate, or nonwoven fabric, to which super absorbent polymers are optionally admixed or fixed. The absorbent body 13 may optionally be wrapped in liquid-pervious liquid-holding wrapping sheet 14, such as crepe paper, for maintaining its shape and the polymer therein.

The absorbent body 13 is formed generally in an hourglass shape having, in the crotch portion, narrower portion 13N with a width narrower than those of the front and back side portions. The dimensions of the narrower portion 13N may suitably be decided; its length in the front-back direction may be about 20 to 50% of the entire length of the diaper, and the width of its narrowest portion may be about 40 to 60% of the entire width of the absorbent body 13. With such a narrower portion 13N, and the planar shape of the inner member 10 being substantially rectangular, no-absorbent side portions 17 without the absorbent body 13 are formed in the portions of the inner member 10 corresponding to the narrower portion 13N of the absorbent body 13.

The liquid impervious sheet 12, together with the top sheet 11, is folded back onto the back surface side on both sides of the width of the absorbent body 13. As the liquid impervious sheet 12, an opaque sheet may preferably be used so as not to show the brown color of feces and urine. For opacification, pigments or fillers, such as calcium carbonate, titanium oxide, zinc oxide, white carbon, clay, talc, and barium sulfate, are internally added to plastics, which is formed into films and preferably used.

On each side portion of the inner member 10, three-dimensional gather 90 is formed that fits on and around the leg. Each three-dimensional gather 90 has, as shown in FIGS. 5 and 6, fixed portion 91 fixed to each side portion of the back surface of the inner member 10, main body portion 92 extending from the fixed portion 91 through the side of the inner member 10 to above the corresponding side portion of the front surface of the inner member 10, laid-down portions 93 formed by each of the front and back end portions of the main body portion 92 fixed in a laid-down state to the corresponding side portion of the front surface of the inner member 10 (top sheet 11 in the illustrated embodiment), and free portion 94 formed between the laid-down portion 93 without the fixing. Each of these portions is formed of gather sheets 95, which are duplicate sheets formed by folding a sheet, such as of non-woven fabric. The gather sheets 95 are fixed to the inner member 10 all along its front-back direction, with the laid-down portions 93 being arranged forward and backward of the no-absorbent side portion 17, and the free portion 94 extending to the front and back sides of the no-absorbent side portion 17. Between the duplicate gather sheets 95, gather elastic members 96 are arranged at positions including the tip of the free portion. In the finished product, as shown in FIG. 5, the gather elastic members 96 function to raise the free portions 94 by means of their elastic contraction force.

The fixed structure of the gather elastic members 96 and the gather sheets 95 are not particularly limited and, for example, a structure of an embodiment shown in FIGS. 5 and 5 may be adopted wherein, in the portions other than the laid-down portions 93, the gather elastic members 96 are adhered and fixed to the gather sheets 95 with a hot melt adhesive arranged at the positions of the gather elastic members 96, and the facing surfaces of the gather sheets 95 are adhered to each other, whereas in the laid-down portions 93, no hot melt adhesive is arranged at the positions of the gather elastic members 96, so that the gather elastic members 96 are not adhered to the gather sheets 95, and the facing surfaces of the gather sheets 95 are not adhered to each other at the positions of the gather elastic members 96.

The gather elastic members 96 may be of a generally used material, such as styrene rubber, polyolefin rubber, urethane rubber, ester rubber, polyurethane, polyethylene, polystyrene, styrene-butadiene, silicone, or polyester. Further, for not being observed readily from outside, it is preferred that the gather elastic members 96 have a thickness of 925 dtex or less and are arranged at a tension of 150 to 350% and at intervals of 7.0 mm or less. In addition, the gather elastic members 96 may be in the form of strings as shown in the drawings, or in the form of tapes having a certain width.

The gather sheets 95 may be selected from various nonwoven fabric and particularly, nonwoven fabric having a limited basis weight and excellent air permeability is preferred for preventing stuffiness. Further, the gather sheets 95 may preferably be of water-repelling nonwoven fabric with a coating of a silicone-based, paraffin-metal-based, or alkyl chromic chloride-based water repelling agent for preventing permeation of urine or the like as well as for preventing rash and improving a touch to the skin (dryness).

As shown in FIGS. 3 to 6, the inner member 10 is bonded on its back surface to the internal surface of the outer member 20 in inner-outer fixed region 10B (hatched region) with a hot melt adhesive or the like. The inner-outer fixed region 10B may suitably be decided, and may cover almost all of the width direction WD of the inner member 10, but preferably is not fixed to the outer member 20 on both ends thereof in the width direction.

Structural Example of Outer Member

The outer member 20 has at least lower torso portion T of the front body F and lower torso portion T of the back body B and, in the illustrated embodiment, further has intermediate portion L, which is a front-back area between the lower torso portion T of the front body F and the lower torso portion T of the back body B. In the crotch portion, the side edge portions of the outer member 20 may be located either closer to the center in the width direction than the side edge portions of the inner member 10 as shown in the drawings, or further outward in the width direction than the side edge portions of the inner member 10.

The outer member 20 in the illustrated embodiment, except for the middle region in the front-back direction of the intermediate portion L thereof, has elastic sheet stretchable structure 20X wherein elastic sheet 30 is interposed between first sheet layer 20A and second sheet layer 20B as shown in FIG. 2 and FIGS. 4 to 6, and the first sheet layer 20A and the second sheet layer 20B are joined through joining holes 31 penetrating the elastic sheet 30 at multiple joining portions 40 arranged at intervals as shown in FIG. 9. The regions having this elastic sheet stretchable structure have stretchable regions contracted in the width direction due to contraction of the elastic sheet 30 and stretchable in the width direction (i.e., the stretchable direction ED is the width direction WD of the diaper).

The planar shape of the outer member 20 is formed with concave around-leg lines 29 so that each side edge in the width direction of the intermediate portion L forms a leg opening, and is hourglass-like shape as a whole. The outer member 20 may be formed of separate front body F and back body B, which are arranged in the crotch portion spaced apart from each other in the front-back direction LD of the diaper.

In the embodiment shown in FIGS. 1 and 2, the elastic sheet stretchable structure 20X is extended to waist end portions 23. Since adoption of the elastic sheet stretchable structure 20X to the waist end portions 23 may result in insufficient tightening at the waist end portions 23, as necessary, the waist end portions 23 may be provided with a stretchable structure of conventional elongated waist portion elastic members 24, without the elastic sheet stretchable structure 20X, as shown in FIGS. 7 and 8. The waist portion elastic members 24 are elongate elastic members, such as a plurality of rubber threads, arranged at intervals in the front-back direction LD, and provide stretchable force to constrict the torso of the body. The waist portion elastic members 24 are not arranged substantially as one bundle with little intervals, but three or more, preferably five or more of them are arranged at intervals of about 3 to 8 mm in the front-back direction to form a prescribed stretchable zone. The stretch rate of the waist portion elastic members 24 when fixed may suitably be decided, and may be about 230 to 320% for ordinary adults. As the waist portion elastic members 24, rubber threads are used in the illustrated embodiment, but other elongate elastic members, such as flat rubber bands, may also be used. Though not shown in the drawings, the waist end portions 23 may be provided with the elastic sheet 30 and also the elongate waist portion elastic members 24 at the locations overlapping the elastic sheet 30, to thereby provide a stretchable structure employing both of the elastic members. Further, in the illustrated embodiment, the edge portions of the leg openings of the outer member 20 are not provided with elongate elastic members extending along the leg openings, but these portions may be provided with elongate elastic members at the locations overlapping the elastic sheet 30, or in place of the elastic sheet 30 in these portions.

Alternatively, though not shown in the drawings, appropriate modifications may be made; for example, the elastic sheet stretchable structure 20X is not provided in the intermediate portion L between the lower torso portion T of the front body F and the lower torso portion T of the back body B; the elastic sheet stretchable structure 20X is provided continuously in the front-back direction LD from the lower torso portion T of the front body F through the intermediate portion L to the lower torso portion T of the back body B; or the elastic sheet stretchable structure 20X is provided only either in the front body F or the back body B.

Stretchable Region

The regions of the outer member 20 having the elastic sheet stretchable structure 20X have stretchable regions stretchable in the width direction WD. The stretchable regions 80 are contracted in the width direction WD due to contraction of the elastic sheet 30 and stretchable in the width direction WD. More specifically, such stretchability may be imparted by means of formation of the elastic sheet stretchable structure 20X by, with the elastic sheet 30 being stretched in the width direction WD, joining the first sheet layer 20A and the second sheet layer 20B through the joining holes 31 in the elastic sheet 30 at intervals in the width direction WD and in the front-back direction LD orthogonal thereto (direction LD orthogonal to the stretchable direction) to thereby form multiple sheet joining portions 40, and by means of arrangement of the sheet joining portions 40 such that the elastic sheet 30 remains continuous in the width direction WD in the stretchable regions 80 and the first sheet layer 20A and the second sheet layer 20B are contracted due to the contraction force of the elastic sheet 30 to form contracted ridges 25.

The stretchable regions 80 may have portions 32 wherein the elastic sheet 30 extends linearly continuously along the width direction WD as in the embodiment shown in FIG. 9, or may not have the portions 32 as in the embodiment shown in FIG. 11 and the embodiment shown in FIG. 15.

In the stretchable regions 80 in the natural length state, the first sheet layer 20A and the second sheet layer 20B between the sheet joining portions 40 are puffed in the directions away from each other to form contraction ridges 25 each extending in the front-back direction LD as shown in FIGS. 9 and 14(b), and in the worn state in which the stretchable regions 80 are stretched to some extent in the width direction WD, the ridges 25F are stretched but remain. Further, in the embodiment shown in the drawings, the first sheet layer 20A and the second sheet layer 20B are not joined with the elastic sheet 30 except for at least the first sheet layer 20A and the second sheet layer 20B at the sheet joining portions 40, as can be seen from FIG. 9(c) simulating the worn state and FIG. 9(a) simulating the spread state of the first sheet layer 20A and the second sheet layer 20B. In such states, the edge of each joining hole 31 in the elastic sheet 30 is displaced away from the circumferential edge of each corresponding sheet joining portion 40 in the stretchable direction to open the vent hole 33 (gap), which imparts air permeability even when the material of the elastic sheet 30 is an imperforate film or sheet. In particular, with the portions 32 wherein the elastic sheet 30 extends linearly continuously along the width direction WD, the joining holes 31 are narrowed due to further contraction of the elastic sheet 30 in the natural length state, resulting in little gaps between each joining hole 31 and each corresponding sheet joining portion 40, whereas without the portions wherein the elastic sheet 30 extends linearly continuously along the width direction WD, the vent holes 33 remain.

The stretchable regions 80 preferably have a maximum elongation in the width direction WD of 190% or more (preferably 200 to 220%). The maximum elongation of the stretchable regions 80 is virtually decided by the stretch rate of the as-manufactured elastic sheet 30, but is lowered from this base stretch rate by the factors that limit contraction in the width direction WD. A major limiting factor is the rate of the length L of the sheet joining portions 40 occupying the unit length in the width direction WD, and the larger this rate, the lower the maximum elongation. Usually, the length L of the joining portions 40 is related to the area rate of the sheet joining portions 40, so that the maximum elongation of the stretchable regions 80 may be adjusted by the area rate of the joining portions 40.

When the stretchable regions 80 have the portions 32 wherein the elastic sheet 30 is linearly continuous along the width direction WD as in the embodiment shown in FIG. 9, the stretching stress of the stretchable regions 80 may be adjusted generally by the sum of the orthogonal dimension $32w$ of the portions 32 (see FIG. 9(a)) wherein the elastic sheet 30 is linearly continuous along the width direction WD (equivalent to the spaced intervals $31d$ between the joining holes 31). In contrast, when the stretchable regions 80 have no portions wherein the elastic sheet 30 is linearly continuous along the width direction WD as in the embodiment shown in FIG. 11 and the embodiment shown in FIG. 15, the stretching stress of the stretchable regions 80 may be adjusted by the angle of intersection between the stretchable direction ED and the continuous direction of unjoined zones 51, 52 wherein a portion without the sheet joining portions continuously extends, and usually the acute angles of intersection $\theta 1$, $\theta 2$ formed between the stretchable direction ED and the continuous direction of each of the unjoined zones 51, 52, respectively, in the spread state are preferably in the range of larger than 0 degree and not larger than 45 degrees, particularly in the range of 10 to 30 degrees.

The area rate of the sheet joining portions 40 and the area of each sheet joining portion 40 in the stretchable regions 80 may suitably be decided, and the following ranges are usually preferred:
Area of each sheet joining portion 40: 0.14 to 3.5 mm² (particularly 0.14 to 1.0 mm²)
Area rate of sheet joining portions 40: 1.8 to 19.1% (particularly 1.8 to 10.6%).

In this way, since the maximum elongation and the stretching stress of the stretchable regions 80 may be adjusted by the areas of the sheet joining portions 40, the stretchable regions 80 may be provided with a plurality of sections with different area rates of the sheet joining portions 40 as shown in FIG. 7, to vary fitting at different sites. In the embodiment shown in FIG. 7, edge regions 82 along the leg openings are made to have a higher area rate of the sheet joining portions 40 compared to the remaining regions, and thus have a lower stretching stress and stretch and contract flexibly.

The shapes of each sheet joining portion 40 and each joining hole 31 in the natural length state may suitably be decided, and may be an arbitrary shape, for example, exact circle, ellipse, polygon, such as triangle, rectangle (see FIG. 9, FIG. 11, and FIG. 15), or diamond (see FIG. 10(b)), or a convex lens shape (see FIG. 10(a)), a concave lens shape (see FIG. 10(c)), a star shape, or a cloud shape. The dimensions of each sheet joining portion is not particularly limited, and its maximum length $40y$ (substantially equal to orthogonal dimension $31y$ of joining hole 31) is preferably 0.5 to 3.0 mm, particularly 0.7 to 1.1 mm, while its maximum width $40x$ is preferably 0.1 to 3.0 mm, and particularly 0.1 to 1.1 mm when the shape is elongated in the direction XD orthogonal to the stretchable direction.

The layout pattern of the sheet joining portions 40 in the stretchable regions 80 is not particularly limited, and various patterns (see, e.g., Patent Literature 1 to 8) may be adopted. In particular, it is preferred that the unjoined zones wherein the portions without the sheet joining portions continuously extend are arranged in a diagonal lattice pattern, as in the embodiment shown in FIG. 11 and the embodiment shown in FIG. 15. The illustrated are the particularly preferred embodiments, wherein in the stretchable regions 80, as the unjoined zones 51, 52 wherein the portions without the sheet joining portions 40 continuously extend, first unjoined zones 51 extending linearly continuously along first direction 51*d* intersecting the stretchable direction ED at an acute angle (acute angle of intersection θ1) is repeatedly present at intervals in the direction orthogonal to the first direction 51*d*. Further, between the adjacent first unjoined zones 51 in the stretchable regions 80, multiple sheet joining portions 40 and multiple joining holes 31 are disposed at intervals. Characteristically, a unit structure including a plurality of first unjoined zones 51 of different first widths 51*w*, each of which is defined as a width in the direction orthogonal to the first direction 51*d*, is repeatedly present in the direction orthogonal to the first direction 51*d* in the stretchable regions 80.

In this way, when the unit structure including a plurality of first unjoined zones 51 of different first width 51*w* is repeatedly present in the direction orthogonal to the first direction 51*d* in the stretchable regions 80, width change of corresponding magnitude relation is also formed in the continuous portions of the elastic sheet 30 inside the first unjoined zones 51. That is, when the width 51*w* of the first unjoined zones 51 is narrow, the width of the continuous portions of the elastic sheet 30 inside thereof is also narrow, whereas when the width 51*w* of the first unjoined zones 51 is wide, the width of the continuous portions of the elastic sheet 30 inside thereof is also wide. With a variety of the first widths 51*w* in the continuous portions of the elastic sheet 30 inside the first unjoined zones 51, both the wider continuous portions of the elastic sheet 30 inside the first unjoined zones 51 and the narrower continuous portions of the elastic sheet 30 inside the first unjoined zones 51 are visually emphasized, and as a result, the stretchable regions 80, even in the natural length state (see FIGS. 13 and 17) or in the worn state stretched to some extent, present aesthetic appearance of oblique stripes. In other words, in the state of contraction to some extent, the sizes of the contraction ridges 25 in the first unjoined zones 51 change depending on the first widths 51*w* of the first unjoined zones 51, so that the oblique stripes more clearly emerge due to the contraction ridges 25.

The unit structure mentioned above is not particularly limited by the magnitude of the sizes of the widths 51*w*, as long as the unit structure includes a plurality of first unjoined zones 51 of different first widths 51*w*, and the first width 51*w* of a first unjoined zone 51 is preferably 1.2 to 60 times as large, or 0.01 to 0.8 times as small as the first width 51*w* of the nearest first unjoined zone 51.

Further, in the above-mentioned unit structure, as long as the unit structure includes a plurality of first unjoined zones 51 of different first widths 51*w*, the first widths 51*w* of all the first unjoined zone 51 may be different, or the first widths 51*w* of part of and a plurality of the first unjoined zones 51 are different from the first widths 51*w* of the remaining one or more first unjoined zones 51.

Even when the oblique stripes along the first direction 51*d* of the contraction ridges 25 of the first unjoined zones 51 and the continuous portions of the elastic sheet 30 inside thereof emerge in the stretchable regions 80, if oblique strips along another oblique direction are more strongly recognized visually in the same stretchable region 80, the oblique strips of the contraction ridges 25 and the continuous portions of the elastic sheet 13 inside thereof may disadvantageously be obscured. In contrast, when the maximum value of the first widths 51*w* of the first unjoined zones 51 is the maximum value of the widths in the direction orthogonal to the continuous directions of all the unjoined zones 51, 52 of the same or different slant directions, the oblique stripes of the contraction ridges 25 of the first unjoined zones 51 and the continuous portions of the elastic sheet 30 inside thereof are more strongly recognized visually in the stretchable regions 80, which is preferred. Here, the maximum value of the first widths 51*w* of the first unjoined zones 51 may suitably be decided, and is preferably 1.2 to 60 times the first width 51*w* of the nearest first unjoined zone 51. With any of the unjoined zones 51, 52 including the first unjoined zones 51, the widths in the direction orthogonal to the continuous direction are not limited, and are usually within the preferred range of 0.02 to 5 mm. It is indisputable that the width in the direction orthogonal to the continuous direction of the unjoined zones 51, 52 is the first width 51*w* for the first unjoined zones 51, and is fixed as the zones are linearly continuous.

First intervals 51*s*, each of which is defined as an interval between first unjoined zones 51 adjacent in the direction orthogonal to the first direction 51*d* may suitably be decided. Thus, the first intervals 51*s* may be the same as, wider than, or narrower than the first widths 51*w* of the adjacent first unjoined zones 51. A preferred example is an embodiment wherein the maximum value of the first widths 51*w* of the first unjoined zones 51 is smaller than the maximum value of the first intervals 51*s* in the unit structure. In this way, by forming wider interval portions in the unit structure, the oblique stripes of the contraction ridges 25 of the first unjoined zones 51 and the continuous portions of the elastic sheet 30 inside thereof are more strongly recognized visually. Here, the maximum value of the first widths 51*w* of the first unjoined zones 51 may suitably be decided, and is preferably 0.01 to 9 times the maximum value of the first intervals 51*s*. The intervals in the direction orthogonal to the continuous directions of all the unjoined zones 51, 52 including the first unjoined zones 51 are not particularly limited, and are usually within a preferred range of 0.3 to 50 mm. Obviously, the intervals in the direction orthogonal to the continuous directions of the unjoined zones 51, 52 mean the first intervals 51*s* as for the first unjoined zones 51, and are constant in the continuous direction.

In the stretchable regions 80, as the unjoined zones 51, 52, second unjoined zones 52 extending linearly continuously along second direction 52*d*, other than the first direction 51*d*, intersecting the stretchable direction ED at an acute angle (acute angle of intersection θ2) may repeatedly be present at intervals in the direction orthogonal to the second direction 52*d*, or the second unjoined zone 52 may not be present. A preferred embodiment having the second unjoined zones 52 is the stretchable regions 80 having the unjoined zones 51, 52 formed in a diagonal lattice pattern, wherein the first unjoined zones 51 extend continuously in one of the directions of the diagonal lattice of the unjoined zones 51, 52, while the second unjoined zones 52 extend continuously in the other of the diagonal lattice of the unjoined zones 51, 52. Here, the first direction 51*d* and the second direction 52*d* have opposite positive/negative inclinations with respect to the stretchable direction ED. Even with the embodiments without the unjoined zones 51, 52 extending continuously in the width direction WD (the stretchable direction ED) like the embodiment shown in FIG. 11 and the embodiment shown in FIG. 15, stretchability in the stretchable regions 80 may sufficiently be secured by respectively setting the acute angles of intersection θ1, θ2 of the first direction 51d and the second direction 52d with respect to the stretchable direction ED to 5 to 45 degrees, particularly 10 to 30 degrees, in the spread state of the stretchable regions 80.

In this regard, however, the oblique stripes of the contraction ridges 25 of the first unjoined zones 51 and the continuous portions of the elastic sheet 30 inside thereof may disadvantageously be obscured if the oblique stripes of the second unjoined zones 52 along the oblique direction in the same stretchable region 80 is visually recognized more strongly. Thus, when the second unjoined zones 52 are present as in the embodiment shown in FIG. 15, it is preferred to arrange the sheet joining portions 40 such that all of the second widths 52w, each of which is defined as a width in the direction orthogonal to the second direction of the second unjoined zones 52, are the same or no second unjoined zone 52 is present. In this way, the oblique stripes of the contraction ridges 25 of the first unjoined zones 51 and the continuous portions of the elastic sheet 30 inside thereof are visually recognized more strongly in the stretchable regions 80.

On the other hand, the sheet joining portions 40 are aligned in the first direction 51d between the adjacent first unjoined zones 51. Here, for example as shown in FIG. 16, it is preferred that all the sheet joining portions 40 are arranged such that the acute angle of interaction θ3 between their longitudinal direction and the direction orthogonal to the stretchable direction ED is not larger than 10 degrees, and formed in elongate shapes with the maximum dimension 40e in the stretchable direction ED of 0.1 to 0.4 mm, which allows larger dimensions of the first unjoined zones 51 in the stretchable direction ED to be secured to suppress lowering of stretchability.

Further, as in the embodiment shown in FIG. 11, when a plurality of wider first unjoined zones 51 with the maximum first width 51w and a plurality of narrower first unjoined zones 51 with the first width 51w narrower than this are arranged respectively adjacent to each other in the direction orthogonal to the first direction 51d in the unit structure, it is preferred that, between the adjacent wider first unjoined zones 51, the sheet joining portions 40 are aligned in the first direction 51d at intervals, which sheet joining portions 40 are arranged with the acute angle of intersection of not larger than 5 degrees between their longitudinal direction and the second direction 52d, and formed in elongate shapes with the maximum dimension 40f in the direction orthogonal to their longitudinal direction of 0.1 to 0.4 mm. Further, it is preferred that, between the adjacent narrower first unjoined zones 51, the sheet joining portions 40 are aligned in the first direction 51d at intervals, which sheet joining portions 40 are arranged with the acute angle of intersection θ3 of 45 degrees or larger between their longitudinal direction and the first direction 51d, and formed in elongate shapes with the maximum dimension 40g in the direction orthogonal to their longitudinal direction of 0.1 to 0.4 mm. With such shapes and arrangements of the sheet joining portions 40, the ridges 25 of the first unjoined zones 51 and the continuous portions of the elastic sheet 30 inside thereof are particularly visually emphasized with a smaller area of the sheet joining portions 40.

The line of the sheet joining portions 40 located between the adjacent unjoined zones 51, 52 (the line in the continuous direction of the unjoined zones 51, 52) may be a single line or a plurality of lines. The sheet joining portions 40 are aligned in the direction of the line preferably at regular intervals, but all the intervals are not necessarily constant, and part of the intervals may be different.

(Non-Stretchable Region)

The regions of the outer member 20 having the elastic sheet stretchable structure 20X may be provided with a non-stretchable region 70 on at least one of the sides in the width direction of the stretchable regions 80, as shown in FIG. 7. A non-stretchable region 70 means that the maximum elongation in the stretchable direction of the region is 120% or less. The maximum elongation of the non-stretchable region 70 is preferably 110% or less, more preferably 100%. The arrangement of the stretchable regions 80 and the non-stretchable regions 70 may suitably be decided. In the case of the outer member 20 of an underpants-type disposable diaper of this embodiment, since the regions overlapping the absorbent body 13 are not required to be stretchable, it is preferred to make part or all of the regions overlapping the absorbent body 13 (preferably including most of the inner-outer fixed region 10B) the non-stretchable regions 70, as in the illustrated embodiment. It is indisputable that the non-stretchable regions 70 may be arranged from the region overlapping the absorbent body 13 toward the region not overlapping the absorbent body 13 located in the width direction WD or the front-back direction LD to the overlapping region, or may be arranged only in the regions not overlapping the absorbent body 13.

In the non-elastic regions 70, the shape of each sheet joining portion 40 is not particularly limited, and may be selected from the shapes similar to the ones mentioned in regard to the stretchable regions 80.

Further in the non-elastic regions, the area rate of the sheet joining portions 40 and the area of each sheet joining portion 40 may suitably be decided, and may usually be preferred to fall within the following ranges for keeping the non-stretchable regions 70 from becoming hard owing to the small area of each sheet joining portion 40 and the low area rate of the sheet joining portions 40:

Area of each sheet joining portion 40: 0.10 to 0.75 mm² (particularly 0.10 to 0.35 mm²)

Area rate of sheet joining portions 40: 4 to 13% (particularly 5 to 10%)

The non-stretchable regions 70 may be formed by densely arranging the sheet joining portions 40, or the like means, so that the ridges are not formed by contraction of the first sheet layer 20A and the second sheet layer 20B due to the contraction force of the elastic sheet 30. Specific examples of the means for forming the non-stretchable regions 70 may be found in Patent Literatures 3 to 6, for example. FIGS. 25 and 26 illustrate the examples of the non-stretchable regions 70 disclosed in Patent Literature 6. In the non-stretchable regions 70, the joining holes 31 are laid out above a certain density level in a staggered arrangement, and the elastic sheet 30 extends continuously in the stretchable direction ED, but does not extend linearly continuously along the stretchable direction ED in the presence of the joining holes 31. In this case, as shown in FIGS. 25 and 26, the vent holes 33 (gaps) are opened in almost same size either in the natural length state or in the spread state.

(Joint Structure of Sheet Joining Portion)

Joining of the first sheet layer 20A and the second sheet layer 20B at the sheet joining portions 40, when made through the joining holes 31 in the elastic sheet 30, is preferably performed such that the first sheet layer 20A and the second sheet layer 20B are not joined to the elastic sheet 30 except for at least the first sheet layer 20A and the second sheet layer 20B at the sheet joining portions 40.

The means for joining the first sheet layer 20A and the second sheet layer 20B at the sheet joining portion 40 are not particularly limited. For example, the joining of the first sheet layer 20A and the second sheet layer 20B at the sheet joining portions 40 may be made by means of a hot melt adhesive or joining means employing material welding, such as heat sealing or ultrasonic sealing.

When the first sheet layer 20A and the second sheet layer 20B are joined at the sheet joining portions 40 through the joining holes 31 in the elastic sheet 30, the structure of the sheet joining portions 40 formed by material welding may be any of first weld mode wherein the first sheet layer 20A and the second sheet layer 20B are joined only by solidified molten products 20m of most or part of at least one of the first sheet layer 20A and the second sheet layer 20B at the sheet joining portions 40 (see FIG. 18(a)), second weld mode wherein the first sheet layer 20A and the second sheet layer 20B are joined only by solidified molten products 30m of all, most, or part of the elastic sheet 30 at the sheet joining portions 40 (see FIG. 18(b)), and third weld mode, which is the combination of these structures (see FIG. 21(c)). Among these, the second and the third structures are preferred.

Particularly preferred is a structure wherein the first sheet layer 20A and the second sheet layer 20B are joined by the solidified molten products 20m of part of the first sheet layer 20A and the second sheet layer 20B as well as the solidified molten products 30m of all or most of the elastic sheet 30 at the sheet joining portions 40. Incidentally, in the third weld mode shown in FIG. 20(b), among the solidified molten products 20m of the fibers of the first sheet layer 20A and the second sheet layer 20B shown in black, the solidified molten products 30m of the elastic sheet 30 shown in white may be observed, whereas in the first weld mode shown in FIG. 20(a), among the solidified molten products 20m of the fibers of the first sheet layer 20A and the second sheet layer 20B, no solidified welded product of the elastic sheet 30 may be observed.

As in the first weld mode or the third weld mode, when the first sheet layer 20A and the second sheet layer 20B are joined by means of the solidified molten products 20m of most or part of at least one of the first sheet layer 20A and the second sheet layer 20B as an adhesive, it is preferred that part of the first sheet layer 20A and the second sheet layer 20B is not molten, as the sheet joining portions 40 are not hardened.

When the first sheet layer 20A and the second sheet layer 20B are of nonwoven fabric, the joint structure wherein part of the first sheet layer 20A and the second sheet layer 20B are not molten, includes a structure wherein the cores (including not only the cores of composite fibers, but also the central portions of single component fibers) of all the fibers at the sheet joining portions 40 remain while the portions around the cores (including not only the sheathes of composite fibers, but also the surficial portions of single component fibers) are molten, and a structure wherein part of the fibers are not molten at all, but the remaining fibers are molten in their entirety or the cores remain while the portions around the cores are molten.

As in the second weld mode and the third weld mode, use of the solidified molten products 30m of the elastic sheet 30 as an adhesive for joining the first sheet layer 20A and the second sheet layer 20B results in high peel strength. The second weld mode may be formed by interposing the elastic sheet 30 between the first sheet layer 20A and the second sheet layer 20B wherein the melting point of at least one of the first sheet layer 20A and the second sheet layer 20B is higher than the melting point of the elastic sheet 30 and the heating temperature for forming the sheet joining portions 40, and heating under pressure the portions to be the sheet joining portions 40, to thereby melt only the elastic sheet 30.

On the other hand, the third weld mode may be formed by interposing the elastic sheet 30 between the first sheet layer 20A and the second sheet layer 20B wherein the melting point of at least one of the first sheet layer 20A and the second sheet layer 20B is higher than the melting point of the elastic sheet 30 and heating under pressure the portions to be the sheet joining portions 40, to thereby melt at least one of the first sheet layer 20A and the second sheet layer 20B as well as the elastic sheet 30.

In view of the above, the melting point of the elastic sheet 30 is preferably about 80 to 145° C., the melting points of the first sheet layer 20A and the second sheet layer 20B are preferably about 85 to 190° C., particularly preferably 150 to 190° C., and the difference between the melting point of the elastic sheet 30 and the melting points of the first sheet layer 20A and the second sheet layer 20B is preferably about 60 to 90° C. The heating temperature is preferably about 100 to 150° C.

In the second weld mode and the third weld mode, with the first sheet layer 20A and the second sheet layer 20B being of nonwoven fabric, the solidified molten product 30m of the elastic sheet 30 may permeate the fibers all over the thicknesses of the first sheet layer 20A and the second sheet layer 20B at the sheet joining portions 40 as shown in FIG. 19(c). However, higher flexibility of the sheet joining portions 40 may be achieved in the structure in which the permeation is halfway through the thicknesses as shown in FIG. 19(a), or the structure in which the permeation hardly occurs into the fibers of the first sheet layer 20A and the second sheet layer 20B as shown in FIG. 19(b).

FIG. 21 illustrates an example of ultrasonic sealing apparatus preferred for the second weld mode and the third weld mode. In this ultrasonic sealing apparatus, for forming the sheet joining portions 40, the first sheet layer 20A, the elastic sheet 30, and the second sheet layer 20B are fed between the ultrasonic horn 61 and the anvil roll 60 having protrusions 60a on its periphery corresponding to the pattern of the sheet joining portions 40. Here, for example, by setting the feeding transfer rate of the feeding driving roller 63 and the nip roller 62 for feeding the elastic sheet 30 on the upstream side to a slower rate compared to the transfer rate at and after the anvil roll 60 and the ultrasonic horn 61, the elastic sheet 30 is stretched in the MD direction (machine direction, flow direction) to a predetermined stretch rate in the pathway from the nipping position between the feeding driving roller 63 and the nip roller 62 to the sealing position between the anvil roll 60 and the ultrasonic horn 61. The stretch rate of the elastic sheet 30 may be set by selecting the velocity difference between the anvil roll 60 and the feeding driving roller 63, and may be, for example, about 300% to 500%.

The first sheet layer 20A, the elastic sheet 30, and the second sheet layer 20B fed between the anvil roll 60 and the ultrasonic horn 61 are, in the state laid one on top of another in this order, pressed between the protrusions 60a and the ultrasonic horn 61 while heated with the ultrasonic vibration energy from the ultrasonic horn 61, to melt only the elastic sheet 30 or the elastic sheet 30 and at least one of the first sheet layer 20A and the second sheet layer 20B, to thereby form the joining holes 31 in the elastic sheet 30, while the first sheet layer 20A and the second sheet layer 20B are joined through the joining holes 31. Accordingly, in this case, the area rate of the sheet joining portions 40 may be selected by the selection of the size, shape, spaced intervals, arrangement pattern in the roll length direction and the roll circumferential direction, of the protrusions 60a on the anvil roll 60.

The reason for the joining holes 31 to be formed is not necessarily clear, but it is assumed that the portions of the elastic sheet 30 corresponding to the protrusions 60a on the anvil roll 60 are welded and removed from the around to form open holes. In this regard, the portion of the elastic sheet 30 between the joining holes 31 adjacent to each other in the starching-contracting direction ED is, as shown in FIGS. 9(*a*), 12, and 13, is disconnected from the portions on its both sides in the stretchable direction by the joining holes 31 to lose support on its both sides in the contracting direction and, accordingly, contracts more in the area closer to the center in the direction LD orthogonal to the stretchable direction ED until it is balanced on the center in the stretchable direction as far as the continuity in the direction orthogonal to the contracting direction can be maintained, so that the joining holes 31 are expanded in the stretchable direction ED.

The constituting materials of the first sheet layer 20A and the second sheet layer 20B are not particularly limited, and preferably has air permeability. In view of this as well as flexibility, nonwoven fabric is preferably used. The nonwoven fabric, when adopted, preferably has a basis weight of about 10 to 25 g/m². Further, part or all of the first sheet layer 20A and the second sheet layer 20B may be a pair of facing layers formed by folding a sheet of material. For example, as shown in the drawings, in the waist end portions 23, the constituting material located externally may be referred to as the second sheet layer 20B, the folded portion 20C formed by folding the constituting material onto the internal surface side at each waist opening edge may be referred to as the first sheet layer 20A, and the elastic sheet 30 may be interposed therebetween, whereas in the remaining portions, the constituting material located internally may be referred to as the first sheet layer 20A, the constituting material located externally may be referred to as the second sheet layer 20B, and the elastic sheet 30 may be interposed therebetween. It is indisputable that the constituting material of the first sheet layer 20A and the constituting material of the second sheet layer 20B may be separately provided all over the front-back direction LD, and the elastic sheet 30 may be interposed between the constituting material of the first sheet layer 20A and the constituting material of the second sheet layer 20B without folding the constituting materials.

The elastic sheet 30 is not particularly limited, and may be of an elastic film or a stretchable nonwoven fabric, as long as it is a sheet of a thermoplastic resin which elastically stretches and contracts by itself. Further, the elastic sheet 30 may be non-porous, or may be provided with multiple pores or slits for air permeability. In particular, the elastic sheet 30 preferably has a tensile strength in the width direction WD (stretchable direction ED, MD direction) of 8 to 25 N/35 mm, a tensile strength in the front-back direction LD (direction XD orthogonal to the stretchable direction, CD direction) of 5 to 20 N/35 mm, a tensile elongation in the width direction WD of 450 to 1050%, and a tensile elongation in the front-back direction LD of 450 to 1400%. The thickness of the elastic sheet 30 is not particularly limited, and is preferably about 20 to 40 μm.

(Coloring)

As discussed above, the vent holes 33 are formed by displacement of the edge of each joining hole 31 away from the circumferential edge of each sheet joining portion 40 in the stretchable direction ED, and thus deformed as the elastic sheet 30 stretches and become larger towards the spread state. Depending on the shape (for example, circular) of the sheet joining portions 40, the edge of each joining hole 31 may be in close contact with the circumferential edge of each sheet joining portion 40 in the natural length state to sometimes form no vent hole 33. Even in this case, in a certain stretched state, such as in a worn state, the vent holes 33 are opened at least on both sides in the stretchable direction ED of the sheet joining portion 40 as the joining hole 31 is stretched in the stretchable direction ED. Since the vent holes 33 are provided for improving air permeability, visual observation of the vent holes by users means imparting of functional aesthetic appearance to the product. It is thus preferred to set the color difference ΔE between the color of the external surface of the elastic sheet 30 and the color of the external surface of the first sheet layer 20A (base sheet layer) to 30 or more so that the shapes of the vent holes 33 are readily observable visually through the second sheet layer 20B (outer sheet layer), as illustrated in FIGS. 12 and 13, 16 and 17, and 22 and 23, due to the difference between the color of the external surface of the elastic sheet 30 and the color of the portions of the external surface of the first sheet layer 20A observed through the vent holes 33. The color difference ΔE between the color of the external surface 30s of the elastic sheet 30 and the color of the external surface 20s of the first sheet layer 20A is particularly preferably 40 or more.

The region wherein the color difference ΔE between the color of the external surface 30s of the elastic sheet 30 and the color of the external surface 20s of the first sheet layer 20A is 30 or more (referred also to the region of improved aesthetic appearance hereinbelow) may be all of the regions having the elastic sheet stretchable structure 20X, or part of those regions, such as the exposed portions exposed externally. In this regard, however, the region of improved aesthetic appearance preferably includes one or a plurality of the vent holes 33 (preferably the joining holes 31) in their entirety. The region of improved aesthetic appearance may be provided in either or both of the stretchable regions 80 and the non-stretchable regions 70. Further, the region of improved aesthetic appearance may be provided at a plurality of locations at intervals, or a plurality of regions of improved aesthetic appearance with different color differences may be provided at intervals or juxtaposed. For example, the stretching regions 80 and the non-stretching regions may be provided with the regions of improved aesthetic appearances with different color differences, or the waist end portion 23 regions and the remaining regions may be provided with the regions of improved aesthetic appearance with different color differences.

This kind of products are sold in the natural length state, and without the openings in the elastic sheet 30 in the natural length state, the aesthetic appearance associate with improved air permeability cannot be perceived unless the products are stretched. Thus, it is preferred that the vent holes 33 are opened in the natural length state as in the stretchable regions 80 illustrated in FIGS. 12 and 13, 16 and 17, and 22 and 23, and in the non-stretchable regions 70 illustrated in FIGS. 25 and 26.

The pattern of the joining holes 31 is not particularly limited, and when the unjoined zones 51, 52 wherein the portions without the sheet joining portions 40 extend continuously are present in a diagonal lattice pattern as in the embodiments shown in FIGS. 12 and 13, 16 and 17, and 22 and 23, the joining holes 31 are arranged accordingly. As a result, the elastic sheet 30 is present in the diagonal lattice pattern (the first unjoined zones 51 and the second unjoined zones 52 intersect obliquely), and visually recognizable readily due to the above-mentioned color difference to provide excellent aesthetic appearance in the diagonal lattice pattern, which is preferable.

For adjusting the color difference ΔE between the color of the external surface 30s of the elastic sheet 30 and the color of the external surface 20s of the first sheet layer 20A, either one or both of the elastic sheet 30 and the first sheet layer 20A may be colored. The method for coloring is not particularly limited, and coloring of a single material into a plurality of colors may be carried out by means of printing or piece-dyeing, whereas coloring of the entire material into a single color may also be carried out by means of printing or piece-dyeing, but means of mixing of dyes or pigments in the stock material (so called spin-dyeing. For example, nonwoven fabric is produced from spun-dyed fibers obtained by coloring the spinning solution with dyes or pigments before spinning) may be adopted.

FIG. 24(a) shows an example of the elastic sheet 30 having on its external surface 30s colored layer 100 colored by printing, and FIG. 24(b) shows an example of the elastic sheet 30 colored by spin-dyeing, whereas FIG. 24(c) shows an example of the first sheet layer 20A having on its external surface 20s colored layer 100 colored by printing, and FIG. 24(d) shows an example of the first sheet layer 20A colored by spin-dyeing. The example shown in FIG. 24(c) in particular simulates the case wherein the first sheet layer 20A is of nonwoven fabric, and the colored layer 100 is provided not only on the external surface 20s but also into inside of the first sheet layer 20A due to permeation of the ink. The first sheet layer 20A is colored all over its thickness direction in the example shown in FIG. 24(d), but may alternatively be colored only partly in its thickness direction by making the first sheet layer 20A with a composite nonwoven fabric and spin-dyeing only part of its layers (e.g., the layer including the external surface 20s).

When either one or both of the elastic sheet 30 and the first sheet layer 20A are to be colored, only the regions of improved aesthetic appearance may be colored, or boarder regions including the regions of improved aesthetic appearance, for example, the overall material, may be colored. When a plurality of regions of improved aesthetic appearance are provided, coloring may differ for each region of improved aesthetic appearance.

The color of the external surface 30s of the elastic sheet 30 and the color of the external surface 20s of the first sheet layer 20A may suitably be decided. For example, when the first sheet layer 20A is to be colored, it is preferred that the coloring of the first sheet layer 20A has a CIELAB L* value of 20 to 60, and an absolute value of at least one of a* and b* values is 0 to 40, while the color of the external surface 30s of the elastic sheet 30 has a CIELAB L* value of 50 to 90, and an absolute value of at least one of a* and b* values is 0 to 40. In this case, as shown in FIGS. 22 and 23 as well as FIG. 26, the color of the external surface 30s of the elastic sheet 30 is white or a pale color close to white, while the color of the external surface 20s of the first sheet layer 20A is deeper (shown dotted in the figures) than that of the elastic sheet 30, so that the vent holes 33 are observed in a deeper color while the remaining portions are observed in a lighter color, resulting in a net-like appearance. Thus, this coloration is suitable for imparting a light tone to the product external surface due to the net-like continuity of white color or a pale color close to white. In addition, this coloration may be realized simply by coloring the first sheet layer 20A without coloring the elastic sheet 30 (i.e., in the material color per se).

When the elastic sheet 30 is to be colored, it is preferred that the coloring of the elastic sheet 30 has a CIELAB L* value of 20 to 60, and an absolute value of at least one of a* and b* values is 0 to 40, while the color of the external surface 20s of the first sheet layer 20A has a CIELAB L* value of 50 to 90, and an absolute value of at least one of a* and b* values is 0 to 40. In this case, as shown in FIGS. 12 and 13 and FIGS. 16 and 17, the color of the external surface 20s of the first sheet layer 20A is white or a pale color close to white, while the color of the external surface 30s of the elastic sheet 30 is deeper than that of the first sheet layer 20A, so that the vent holes 33 are observed in a lighter color while the remaining portions are observed in a deeper color (shown dotted in the figures), resulting in a net-like appearance. Thus, this coloration is suitable for imparting a deep or dark tone due to the net-like continuity of a deep color. In addition, this coloration may be realized simply by coloring the elastic sheet 30 without coloring the first sheet layer 20A (i.e., in the material color per se), and is thus preferable.

The translucency of the second sheet layer 20B is not particularly limited as long as the color of the external surface 30s of the elastic sheet 30 and the color of the portions of the external surface 20s of the first sheet layer 20A observed through the vent holes 33 are observable through the second sheet layer 20B, and nonwoven fabric having a transmittance of 50% or higher, particularly 65% or higher according to the translucency provided in JIS L 1913: 2010 (JIS method) is preferred for excellent visibility of the shape of the vent holes 33. The second sheet layer 20B is preferably not colored (i.e., in the material color per se), but may be colored.

Definition of Terms in the Description

The following terms in the description shall have the following means unless otherwise specified in the description.

The "front body" and "back body" refer to the portions on the front side and the back side, respectively, of the center in the front-back direction of the underpants-type disposable diaper. The crotch portion refers to the area in the front-back direction including the center in the front-bac direction of the underpants-type disposable diaper and, when the absorbent body has a narrower portion, refers to the area in the front-back direction including the narrower portion.

The "maximum elongation" means the maximum value of elongation in the stretchable direction ED (in other words, the elongation in the spread state in which the first sheet layer and the second sheet layer are spread flatly without contraction or slack), and refers to the length in the spread state expressed in percentage based on the natural length being 100%.

The "area rate" means the rate of the objective portion occupying the unit area, and refers to the value expressed in percentage obtained by dividing the sum of the areas of objective portions (e.g., sheet joining portions 40, openings of the joining holes 31, vent holes) in an objective region (e.g., stretchable regions 80, non-stretchable regions 70) by the area of the said objective region. In particular, the "area rate" in the region having the stretchable structure refers to the area rate in the spread state. When multiple objective portions are provided at intervals, the area rate is preferably determined by setting the objective region to a size containing ten or more of the objective portions.

The "stretch rate" refers to a value based on the natural length being 100%. For example, 200% stretch rate means the same as the two-fold stretch.

The "fineness" is determined as follows. A sample or a test piece is preliminarily dried, and left in a testing room or testing apparatus under the standard conditions (the testing location is at a temperature of 23±1° C. and relative humidity of 50±2%) until it is at constant mass. The preliminary drying refers to making of a sample or a test piece into constant mass in the environment at a temperature of 100° C. Incidentally, fibers having an official regain of 0.0% do not have to be subjected to the preliminary drying. A sample of 100 mm×100 mm in size is cut out of the test piece in constant mass using a sampling template (100 mm×100 mm). The weight of the sample is measured and multiplied by 100 to determine the weight per one square meter, which is taken as the fineness.

The "thickness" of the absorbent body is determined using a thickness gauge manufactured by OZAKI MFG. CO., LTD. (PEACOCK, large dial thickness gauge, Model J-B (measurement range 0 to 35 mm) or Model K-4 (measurement range 0 to 50 mm), with the sample and the thickness gauge leveled.

The "thickness" other than the above is automatically determined using an automatic thickness measurement equipment (KES-G5 handy compression testing program) under the load of 0.098 N/cm² and the compression area of 2 cm².

The "tensile strength" and the "tensile elongation (breaking elongation)" refer to the values determined according to JIS K7127: 1999 "Plastics-Determination of tensile properties" with the initial chuck clearance (gauge line distance) of 50 mm and the tension rate of 300 ram/min, except that the test piece is in a rectangular shape of 35 mm wide by 80 mm long. As a tensile testing machine, for example, AUTOGRAPH AGS-G100N manufactured by SHIMADZU CORPORATION may be used.

The "stretching stress" refers to the tensile stress (N/35 mm) determined in stretching in the elastic region by the tensile test according to JIS K7157: 1999 "Plastics-Determination of tensile properties" with the initial chuck clearance (gauge line distance) of 50 mm and the tension rate of 300 mm/min, and the degree of stretching may suitably be decided depending on the sample to be tested. The test piece is preferably in a rectangular shape of 35 mm wide by 80 mm long or longer, but when a test piece of 35 mm wide cannot be cut out, a test piece is cut out at a possible width and the measured value is converted to the value corresponding to the width of 35 mm. Further, even when the objective region is too small to take a test piece of sufficient size, for the purpose of comparing the magnitude of the stretching stress, comparison is still possible as long as the test pieces of the same size, even if reasonably small, are used. As a tensile testing machine, for example, AUTOGRAPH AGS-G100N manufactured by SHIMADZU CORPORATION may be used.

The L* value, the a* value, and the b* value of the "CIELAB" may be determined according to JIS Z 8781-4 "Part 4: CIE 1976 L*a*b* Colour space" in the following manner. Specifically, the first sheet layer (base sheet layer) and the elastic sheet are taken out respectively and independently as samples. Then using measuring apparatus, such as X-Rite exact Standard (measurement diameter 1.5 mm) manufactured by X-Rite, with a white reflectance standard (white board) arranged on the internal surface of a sample in the spread state, three suitable points on the sample (for the first sheet layer (base sheet layer), the external surface of the portion without the sheet joining portions, and for the elastic sheet, the external surface of the portion without the joining holes) are arbitrarily decided, the L* value, the a* value, and the b* value of each point are measured, and the average value is taken as the measured value. Incidentally, if the measurement diameter of the measuring apparatus is too large with respect to the sheet joining portions and the joining intervals to measure only the portions of the first sheet layer (base sheet layer) without the sheet joining portions or only the portions of the elastic sheet without the joining holes, the L* value, the a* value, and the b* value may be measured using a sample made of a material identical with that of the product. Alternatively, the L* value, the a* value, and the b* value may be determined by cutting out a number of only the portions of the first sheet layer (base sheet layer) without the sheet joining portions and a number of only the portions of the elastic sheet without the joining holes, and arranging and attaching the same on a white reflectance standard (white board) with little gaps or overlapping, or shadow resulting therefrom.

The "color difference ΔE" may be calculated by the following formula based on the above-mentioned measured values of the L* value, the a* value, and the b* value:

$$\Delta E = ((\Delta L^*)^2 + (\Delta a^*)^2 + (\Delta b^*)^2)^{1/2}$$

The "spread state" means the state of flat spread without contraction or slack.

The dimensions of each portion mean the dimensions in the spread state, not in the natural length state, unless otherwise specified.

A test or a measurement is performed in a testing room or testing apparatus under the standard conditions (the testing location is at a temperature of 23±1° C. and relative humidity of 50±2%) unless the environmental conditions are otherwise specified.

INDUSTRIAL APPLICABILITY

The present invention may be applied to a stretchable member in general disposable wearable articles, including, in addition to the underpants-type disposable diapers of the embodiments discussed above, various disposable diapers, such as of tape type or pad type, sanitary napkins, disposable wearable articles for swimming or playing with water, as long as the article has a stretchable region to which the elastic sheet stretchable structure may be applied.

DESCRIPTION OF REFERENCE SIGNS

10: inner member; 10B: inner-outer fixed region; 11: top sheet; 12: liquid impervious sheet; 13: absorbent body; 13N: narrower portion; 14: wrapping sheet; 17: no-absorbent side portion; 20: outer member; 20A: first sheet layer; 20B: second sheet layer; 20C: folded portion; 20X: elastic sheet stretchable structure; 21: side seal portion; 23: waist end portion; 24: waist portion elastic member; 25: contraction ridge; 29: around-leg line; 30: elastic sheet; 31: joining hole; 33: vent hole; 40: sheet joining portion; 51, 52: unjoined zone; 51: first unjoined zone; 51d: first direction; 51s: first interval; 51w: first width; 52: second unjoined zone; 52d:

second direction; 70: non-stretchable region; 80: stretchable region; 90: three-dimensional gather; 93: laid-down portion; 94: free portion; 95: gather sheet; 96: gather elastic member; 100: colored layer; B: back body; ED: stretchable direction; F: front body; L: intermediate portion; LD: front-back direction; T: lower torso portion; WD: width direction.

The invention claimed is:

1. A stretchable member comprising:
an elastic sheet stretchable structure having an outer sheet layer with an exposed portion, a base sheet layer, and an elastic sheet interposed therebetween, the outer sheet layer and the base sheet layer being joined through joining holes penetrating the elastic sheet or via the elastic sheet at multiple sheet joining portions arranged at intervals,
wherein a region having the elastic sheet stretchable structure comprises a stretchable region contracted in a stretchable direction due to contraction of the elastic sheet and stretchable in the stretchable direction,
vent holes each opened at least in a spread state by displacement of an edge of each joining hole away from a circumferential edge of each sheet joining portion in the stretchable direction,
wherein a color of an external surface of the elastic sheet and a color of portions of an external surface of the base sheet layer observed through the vent holes are observable through the outer sheet layer, and
wherein a color difference ΔE between the color of the external surface of the elastic sheet and the color of the external surface of the base sheet layer is 30 or more.

2. The stretchable member according to claim 1,
wherein a region of the external surface of the base sheet layer overlapping at least the exposed portion is entirely colored by printing, or the base sheet layer is colored by spin-dyeing,
wherein coloring of the base sheet layer has a CIELAB L* value of 20 to 60, and an absolute value of at least one of a* and b* values is 0 to 40, and
wherein the color of the external surface of the elastic sheet has a CIELAB L* value of 50 to 90, and an absolute value of at least one of a* and b* values is 0 to 40.

3. The stretchable member according to claim 1,
wherein a region of the external surface of the elastic sheet overlapping at least the exposed portion is entirely colored by printing, or the elastic sheet is colored by spin-dyeing,
wherein coloring of the elastic sheet has a CIELAB L* value of 20 to 60, and an absolute value of at least one of a* and b* values is 0 to 40, and
wherein the color of the external surface of the base sheet layer has a CIELAB L* value of 50 to 90, and an absolute value of at least one of a* and b* values is 0 to 40.

4. The stretchable member according to claim 1,
wherein the outer sheet layer is of nonwoven fabric having a transmittance of 50% or higher according to the translucency provided in JIS L 1913:2010 (JIS method).

5. The stretchable member according to claim 1,
wherein the vent holes in the stretchable region in its natural length are opened.

6. The stretchable member according to claim 5,
wherein in the stretchable region in a spread state, as an unjoined zone wherein a portion without the sheet joining portions continuously extends, a first unjoined zone extending linearly continuously along a first direction intersecting the stretchable direction at an acute angle is repeatedly present at intervals in a direction orthogonal to the first direction,
wherein multiple sheet joining portions and multiple joining holes are disposed at intervals between adjacent first unjoined zones in the stretchable region,
wherein a unit structure comprising a plurality of first unjoined zones of different first widths is repeatedly present in a direction orthogonal to the first direction in the stretchable region, a first width being defined as a width in a direction orthogonal to the first direction,
wherein in the stretchable region in a spread state, as an unjoined zone wherein a portion without the sheet joining portions continuously extends, a second unjoined zone extending linearly continuously along a second direction intersecting the stretchable direction at an acute angle is repeatedly present at intervals in a direction orthogonal to the second direction,
wherein multiple sheet joining portions and multiple joining holes are disposed at intervals between adjacent second unjoined zones in the stretchable region,
wherein a unit structure comprising a plurality of second unjoined zones of different second widths is repeatedly present in a direction orthogonal to the second direction in the stretchable region, a second width being defined as a width in a direction orthogonal to the second direction,
wherein the first direction and the second direction have opposite positive/negative inclinations with respect to the stretchable direction, and
wherein in a spread state of the stretchable region, acute angles of intersection between the stretchable direction and each of the first direction and the second direction is 5 to 45 degrees, respectively.

7. A disposable wearable article comprising:
an outer member integrally extending from a front body to a back body or an outer member having separate front and back bodies;
an inner member attached to an intermediate portion in a width direction of the outer member across front and back sides of a crotch portion;
side seal portions each formed by joining each side portion of the outer member in the front body and each side portion of the outer member in the back body, and
a waist opening and a pair of right and left leg openings,
wherein the outer member in at least one of the front body and the back body is a stretchable member having the elastic sheet stretchable structure according to claim 1, the elastic sheet stretchable structure being arranged over a width direction area corresponding to an area between the side seal portions in at least part of a front-back direction area, with the stretchable direction of the stretchable region arranged in a width direction.

8. The stretchable member according to claim 2,
wherein the outer sheet layer is of nonwoven fabric having a transmittance of 50% or higher according to the translucency provided in JIS L 1913: 2010 (JIS method).

9. The stretchable member according to claim 3,
wherein the outer sheet layer is of nonwoven fabric having a transmittance of 50% or higher according to the translucency provided in JIS L 1913: 2010 (JIS method).

10. The stretchable member according to claim 2,
wherein the vent holes in the stretchable region in its natural length are opened.

11. The stretchable member according to claim 3,
wherein the vent holes in the stretchable region in its natural length are opened.

12. The stretchable member according to claim 4,
wherein the vent holes in the stretchable region in its natural length are opened.

* * * * *